United States Patent
Tojo et al.

(10) Patent No.: US 6,479,689 B1
(45) Date of Patent: Nov. 12, 2002

(54) PROCESS FOR CONTINUOUSLY PRODUCING DIALKYL CARBONATE AND DIOL

(75) Inventors: Masahiro Tojo; Kazuhiro Oonishi, both of Kurashiki (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/857,980

(22) PCT Filed: Mar. 3, 2000

(86) PCT No.: PCT/JP00/01284

§ 371 (c)(1),
(2), (4) Date: Jun. 11, 2001

(87) PCT Pub. No.: WO00/51954

PCT Pub. Date: Sep. 8, 2000

(30) Foreign Application Priority Data

Mar. 3, 1999 (JP) ............................................. 11-055738

(51) Int. Cl.$^7$ ......................... C07C 69/96; C07C 43/11; C07C 31/18
(52) U.S. Cl. ........................ 558/277; 568/619; 568/852
(58) Field of Search .......................... 558/277; 568/619, 568/852

(56) References Cited

U.S. PATENT DOCUMENTS

| 5,231,212 A | 7/1993 | Buysch et al. |
| 5,359,118 A | 10/1994 | Wagner et al. |
| 5,847,189 A | 12/1998 | Tojo et al. |

FOREIGN PATENT DOCUMENTS

| JP | 4-198141 | 7/1992 |
| JP | 9-176061 | 7/1997 |
| JP | 10-36297 | 2/1998 |

*Primary Examiner*—T. A. Solola
*Assistant Examiner*—Joseph Murray
(74) *Attorney, Agent, or Firm*—Pennie & Edmonds LLP

(57) ABSTRACT

A method for continuously producing a dialkyl carbonate and a diol, comprising: (1) continuously feeding a cyclic carbonate and an aliphatic monohydric alcohol to a continuous multi-stage distillation column, and continuously effecting a transesterification between the cyclic carbonate and the aliphatic monohydric alcohol in the presence of a transesterification catalyst in the distillation column, while continuously withdrawing a low boiling point mixture in a gaseous form containing the produced dialkyl carbonate and the unreacted aliphatic monohydric alcohol from an upper portion of the distillation column and continuously withdrawing a high boiling point mixture in a liquid form containing the produced diol and the unreacted cyclic carbonate from a lower portion of the distillation column, and (2) continuously feeding the high boiling point mixture withdrawn from the lower portion of the distillation column to a continuous etherification reactor, to thereby effect a continuous etherification reaction between the unreacted cyclic carbonate and a part of the produced diol and produce a chain ether and carbon dioxide, while continuously withdrawing the resultant etherification reaction mixture containing the remainder of the diol produced in step (1) and the produced chain ether from the continuous etherification reactor, wherein the etherification reaction mixture has a cyclic carbonate content of from 0 to $10^{-2}$ in terms of the weight ratio of the cyclic carbonate to the diol.

12 Claims, 5 Drawing Sheets

PROCESS FOR CONTINUOUSLY PRODUCING DIALKYL CARBONATE AND DIOL

BACKGROUND OF THE INVENTION

The instant application is a 371 of PCT/JP00/01284 filed Mar. 3, 2000.

1. Field of the Invention

The present invention relates to a method for continuously producing a dialkyl carbonate and a diol. More particularly, the present invention is concerned with a method for continuously producing a dialkyl carbonate and a diol from a cyclic carbonate and an aliphatic monohydric alcohol, comprising: (1) continuously feeding a cyclic carbonate and an aliphatic monohydric alcohol to a continuous multi-stage distillation column, and continuously effecting a transesterification between the cyclic carbonate and the aliphatic monohydric alcohol in the presence of a transesterification catalyst in the multi-stage distillation column, while continuously withdrawing a low boiling point mixture in a gaseous form containing the produced dialkyl carbonate and the unreacted aliphatic monohydric alcohol from an upper portion of the multi-stage distillation column and continuously withdrawing a high boiling point mixture in a liquid form containing the produced diol and the unreacted cyclic carbonate from a lower portion of the multi-stage distillation column, and (2) continuously feeding the high boiling point mixture withdrawn from the lower portion of the multi-stage distillation column to a continuous etherification reactor, to thereby effect a continuous etherification reaction between the unreacted cyclic carbonate and a part of the produced diol and produce a chain ether and carbon dioxide, while continuously withdrawing the resultant etherification reaction mixture containing the remainder of the diol produced in step (1) and the produced chain ether from the continuous etherification reactor, wherein the etherification reaction mixture has a cyclic carbonate content of from 0 to $10^{-2}$ in terms of the weight ratio of the cyclic carbonate to the diol. By the method of the present invention, in a continuous process for producing a dialkyl carbonate and a diol from a cyclic carbonate and an aliphatic monohydric alcohol, a high purity diol can be easily obtained.

2. Prior Art

With respect to the method for producing a dialkyl carbonate and a diol by reacting a cyclic carbonate with an aliphatic monohydric alcohol, various proposals have been made. Most of those proposals relate to the development of catalysts for the above reaction. Examples of such catalysts include alkali metals or basic compounds containing alkali metals (see U.S. Pat. No. 3,642,858, Unexamined Japanese Patent Application Laid-Open Specification No. 54-48715 (corresponding to U.S. Pat. No. 4,181,676)), tertiary aliphatic amines (see Unexamined Japanese Patent Application Laid-Open Specification No. 51-122025 (corresponding to U.S. Pat. No. 4,062,884)), thallium compounds (see Unexamined Japanese Patent Application Laid-Open Specification No. 54-48716 (corresponding to U.S. Pat. No. 4,307,032)), tin alkoxides (see Unexamined Japanese Patent Application Laid-Open Specification No. 54-63023), alkoxides of zinc, aluminum and titanium (see Unexamined Japanese Patent Application Laid-Open Specification No. 54-148726), a mixture of a Lewis acid with a nitrogen-containing organic base (see Unexamined Japanese Patent Application Laid-Open Specification No. 55-64550), phosphine compounds (see Unexamined Japanese Patent Application Laid-Open Specification No. 55-64551), quaternary phosphonium salts (see Unexamined Japanese Patent Application Laid-Open Specification No. 56-10144), cyclic amidines (see Unexamined Japanese Patent Application Laid-Open Specification No. 59-106436 (corresponding to U.S. Pat. No. 4,681,967, EP 110629, and DE 3366133G)), compounds of zirconium, titanium and tin (see Unexamined Japanese Patent Application Laid-Open Specification No. 63-41432 (corresponding to U.S. Pat. No. 4,661,609, EP 255252 and DE 3781742G)), a solid, strongly basic anion-exchanger containing a quaternary ammonium group (see Unexamined Japanese Patent Application Laid-Open Specification No. 63-238043), a solid catalyst selected from the group consisting of a tertiary amine- or quaternary ammonium group-containing ion-exchange resin, a strongly acidic or a weakly acidic ion-exchange resin, a silica impregnated with a silicate of an alkali metal or an alkaline earth metal, and a zeolite exchanged with ammonium ion (see Unexamined Japanese Patent Application Laid-Open Specification No. 64-31737 (corresponding to U.S. Pat. No. 4,691,041)), a homogeneous catalyst selected from the group consisting of tertiary phosphine, tertiary arsine, tertiary stibine, a divalent sulfur compound and a selenium compound (see U.S. Pat. No. 4,734,518).

With respect to the method for conducting the above-mentioned reaction between a cyclic carbonate and a diol, the below-mentioned four types of methods (1) to (4) have conventionally been proposed. Hereinbelow, explanation is made with respect to such methods (1) to (4), taking as an example the production of dimethyl carbonate and ethylene glycol by the reaction between ethylene carbonate and methanol, which is a representative example of reactions between cyclic carbonates and diols.

(1) A completely batchwise method (hereinafter referred to as "method (1)").
(2) A batchwise method using a reaction vessel provided at an upper portion thereof with a distillation column (hereinafter referred to as "method (2)").
(3) A liquid flow method using a tubular reactor (hereinafter referred to as "method (3)").
(4) A reactive distillation method (hereinafter referred to as "method (4)").

The completely batchwise method (1) is a method in which ethylene carbonate, methanol and a catalyst are fed to an autoclave as a batchwise reaction vessel, and a reaction is performed at a reaction temperature higher than the boiling point of methanol under pressure for a predetermined period of time (see U.S. Pat. No. 3,642,858, Unexamined Japanese Patent Application Laid-Open Specification No. 54-48715 (corresponding to U.S. Pat. No. 4,181,676, EP 1082 and DE 2860078G), Unexamined Japanese Patent Application Laid-Open Specification No. 54-63023, Unexamined Japanese Patent Application Laid-Open Specification No. 54-148726, Unexamined Japanese Patent Application Laid-Open Specification No. 55-64550, Unexamined Japanese Patent Application Laid-Open Specification No. 55-64551 and Unexamined Japanese Patent Application Laid-Open Specification No. 56-10144).

The batchwise method (2), using an apparatus comprising a reaction vessel provided at an upper portion thereof with a distillation column, is a method in which ethylene carbonate, methanol and a catalyst are fed to the reaction vessel, and a reaction is performed by heating the contents of the reaction vessel to a predetermined temperature. In this method, the produced dimethyl carbonate and methanol form a minimum boiling point azeotropic mixture having a boiling point of 63° C./760 mmHg. The boiling point of methanol per se is 64.6° C./760 mmHg. In this method, the reaction is performed by using an excess amount of methanol in the reaction system, so that the resultant reaction products can be separated into the azeotropic mixture and methanol, due to the difference in boiling point therebetween, by means of the distillation column provided at the upper portion of the reaction vessel. Specifically, a gaseous mixture of dimethyl carbonate and methanol, which is formed in the reaction vessel, is allowed to ascend inside the distillation column, and during the ascending of the gaseous mixture, the gaseous mixture is caused to separate into a gaseous azeotropic mixture and liquid methanol. Then, the gaseous azeotropic mixture is distilled from the top of the distillation column while the liquid methanol flows down to the reaction vessel so as to be recycled to the reaction system in the reaction vessel.

The liquid flow method (3) is a method in which a solution of ethylene carbonate in methanol is continuously fed to a tubular reactor to perform a reaction at a predetermined reaction temperature in the tubular reactor, and the resultant reaction mixture in a liquid form containing the unreacted materials (i.e., ethylene carbonate and methanol) and the reaction products (i.e., dimethyl carbonate and ethylene glycol) is continuously withdrawn through an outlet of the reactor. This method has conventionally been conducted in two different manners in accordance with the two types of catalyst used. That is, one of the manners consists in passing a mixture of a solution of ethylene carbonate in methanol and a solution of a homogenous catalyst in a solvent through a tubular reactor to perform a reaction, thereby obtaining a reaction mixture, and separating the catalyst from the obtained reaction mixture (see Unexamined Japanese Patent Application Laid-Open Specification No. 63-41432 (corresponding to U.S. Pat. No. 4,661,609, EP 255252 and DE 3781742G) and U.S. Pat. No. 4,734,518). The other manner consists in performing the reaction in a tubular reactor having a heterogeneous catalyst securely placed therein (see Unexamined Japanese Patent Application Laid-Open Specification No. 63-238043 and Unexamined Japanese Patent Application Laid-Open Specification No. 64-31737 (corresponding to U.S. Pat. No. 4,691,041, EP 298167 and DE 3781796G)).

The reactive distillation method (4) is a method in which each of ethylene carbonate and methanol is continuously fed to a multi-stage distillation column to perform a reaction in a plurality of stages of the distillation column in the presence of a catalyst, while continuously effecting separation between the produced dimethyl carbonate and the produced ethylene glycol (see Unexamined Japanese Patent Application Laid-Open Specification No. 4-198141, Unexamined Japanese Patent Application Laid-Open Specification No. 4-230243, Unexamined Japanese Patent Application Laid-Open Specification No. 5-213830 (corresponding to DE 4129316, U.S. Pat. No. 5,231,212 and EP 530615) and Unexamined Japanese Patent Application Laid-Open Specification No. 6-9507 (corresponding to U.S. Pat. No. 5,359,118, EP 569812 and DE 4216121)).

However, the above-mentioned conventional methods (1) to (4) have their respective problems as described below.
Problems accompanying methods (1) and (3) In the case of each of the completely batchwise method (1) and the flow method (3) using a tubular reactor, it is impossible to achieve a higher conversion of ethylene carbonate than the conversion of ethylene carbonate at the equilibrium state of reaction (the latter conversion depends on the composition ratio of the feedstocks fed to the reactor and the reaction temperature). For example, in Example 1 of Unexamined Japanese Patent Application Laid-Open Specification No. 63-41432 (corresponding to U.S. Pat. No. 4,661,609, EP 255252 and DE 3781742G) which is directed to a continuous flow reaction method using a tubular reactor and wherein the flow reaction is conducted at 130° C. using a feedstock mixture having a methanol/ethylene carbonate molar ratio of 4/1, the conversion of ethylene carbonate is only 25%. This means that large amounts of unreacted ethylene carbonate and unreacted methanol, which are contained in the reaction mixture, need to be separated and recovered, and in turn recycled to the reactor. Actually, in the method disclosed in Unexamined Japanese Patent Application Laid-Open Specification No. 64-31737 (corresponding to U.S. Pat. No. 4,691,041, EP 298167 and DE 3781796G), various apparatuses are used for the separation, purification, recovery and recycling of the unreacted compounds.
Problems accompanying method (2) As described below in detail, the batchwise method (2) using a reaction vessel provided at an upper portion thereof with a distillation column has problems in that the reaction must be conducted for a prolonged period of time and, therefore, a large amount of methanol needs to be used for preventing the lowering of the selectivity for the desired products.

In method (2), in order to compensate for the methanol distilled as an azeotropic mixture of the methanol and the produced dimethyl carbonate, the continuous or batchwise addition of supplemental methanol to the reaction vessel is optionally conducted. However, irrespective of whether or not such an addition of supplemental methanol is conducted, the reaction per se is performed only in a batch-type reaction vessel. That is, in this method, the reaction is batchwise performed under reflux for a prolonged period of time as long as 3 to 20 hours.

In this method, the dimethyl carbonate, which is one of the reaction products, is continuously withdrawn out of the reaction system, whereas the ethylene glycol, which is another reaction product, remains together with the unreacted ethylene carbonate in the reaction system containing the catalyst for a long period of time. This long residence time of the ethylene glycol and the ethylene carbonate in the reaction system causes side reactions to thereby produce polyethylene glycols, such as diethylene glycol and triethylene glycol. For preventing the occurrence of such side reactions and the lowering of the selectivity for the desired products, it is necessary to use a largely excess amount of methanol, relative to the amount of the ethylene carbonate which is batchwise fed to the reaction vessel. In fact, in the conventionally proposed methods, the following examples are noted in which a largely excess amount of methanol is used; that is, use is made of methanol in excess amounts (in terms of the number of moles of methanol per mole of ethylene carbonate or propylene carbonate), such as 14 moles (U.S. Pat. No. 3,803,201), 17 moles (Unexamined Japanese Patent Application Laid-Open Specification No. 1-311054), 22 moles (Unexamined Japanese Patent Application Laid-Open Specification No. 51-122025 (corresponding to U.S. Pat. No. 4,062,884 and DE 2615665)), and 23 moles (Unexamined Japanese Patent Application Laid-Open Specification No. 54-48716 (corresponding to U.S. Pat. No. 4,307,032, EP 1083 and DE 2860142G)).
Problems accompanying method (4) In the case of the reactive distillation method (4), it is possible to perform a reaction with high conversion, as compared to the conversions in methods (1), (2) and (3). However, needles to say, even in the case of method (4), production of a dialkyl carbonate and a diol is performed by a reversible, equilibrium reaction. Accordingly, even when it is possible to achieve a substantially 100% conversion of a cyclic carbonate by method (4), it is impossible to prevent a trace amount of the cyclic carbonate from remaining unreacted in a produced diol. Therefore, for obtaining a high purity diol by method (4), in general, it is necessary to separate the cyclic carbonate from the diol by performing a distillation under strictly controlled conditions. In WO 97/23445 (corresponding to U.S. Pat. No. 5,847,189 and EP 0889025), it is attempted to solve this problem by hydrolyzing the unreacted cyclic carbonate to convert it into a diol. However, the method of WO 97/23445 needs the use of water in addition to a catalyst and feedstocks used for the transesterification. Further, due to the use of water, it is also necessary to perform a step for removing water, so that the process necessarily becomes complicated.

As can be understood from the above, no method has heretofore been proposed for continuously producing a dialkyl carbonate and a diol from a cyclic carbonate and an aliphatic monohydric alcohol, wherein a high purity diol can be obtained without a need for a complicated separation step or a need for additional materials other than feedstocks and a catalyst in the transesterification.

SUMMARY OF THE INVENTION

The present inventors have made extensive and intensive studies with a view toward developing a method which is free from the above problems accompanying the prior art. As a result, it has unexpectedly been found that the above objective can be achieved by a method for continuously producing a dialkyl carbonate and a diol, comprising: (1) continuously feeding a cyclic carbonate and an aliphatic monohydric alcohol to a continuous multi-stage distillation column, and continuously effecting a transesterification between the cyclic carbonate and the aliphatic monohydric alcohol in the presence of a transesterification catalyst in the multi-stage distillation column, while continuously withdrawing a low boiling point mixture in a gaseous form containing the produced dialkyl carbonate and the unreacted aliphatic monohydric alcohol from an upper portion of the multi-stage distillation column and continuously withdrawing a high boiling point mixture in a liquid form containing the produced diol and the unreacted cyclic carbonate from a lower portion of the multi-stage distillation column, and (2) continuously feeding the high boiling point mixture withdrawn from the lower portion of the multi-stage distillation column to a continuous etherification reactor, to thereby effect a continuous etherification reaction between the unreacted cyclic carbonate and a part of the produced diol and produce a chain ether and carbon dioxide, while continuously withdrawing the resultant etherification reaction mixture containing the remainder of the diol produced in step (1) and the produced chain ether from the continuous etherification reactor, wherein the etherification reaction mixture has a cyclic carbonate content of from 0 to $10^{-2}$ in terms of the weight ratio of the cyclic carbonate to the diol. That is, it has unexpectedly been found that, by the above method, a high purity diol can be easily obtained without a need for a complicated distillation-separation step or a need for additional materials other than feedstocks and a catalyst in the transesterification. The present invention has been made, based on this novel finding.

Accordingly, it is a primary object of the present invention to provide a method for continuously producing a dialkyl carbonate and a diol from a cyclic carbonate and an aliphatic monohydric alcohol, wherein the method enables a high purity diol to be easily obtained without a need for a complicated distillation-separation step or a need for additional materials other than feedstocks and a catalyst in the transesterification.

The foregoing and other objects, features and advantages of the present invention will be apparent from the following detailed description and appended claims taken in connection with the accompanying drawings.

DESCRIPTION OF REFERENCE NUMERALS

Figure 1:
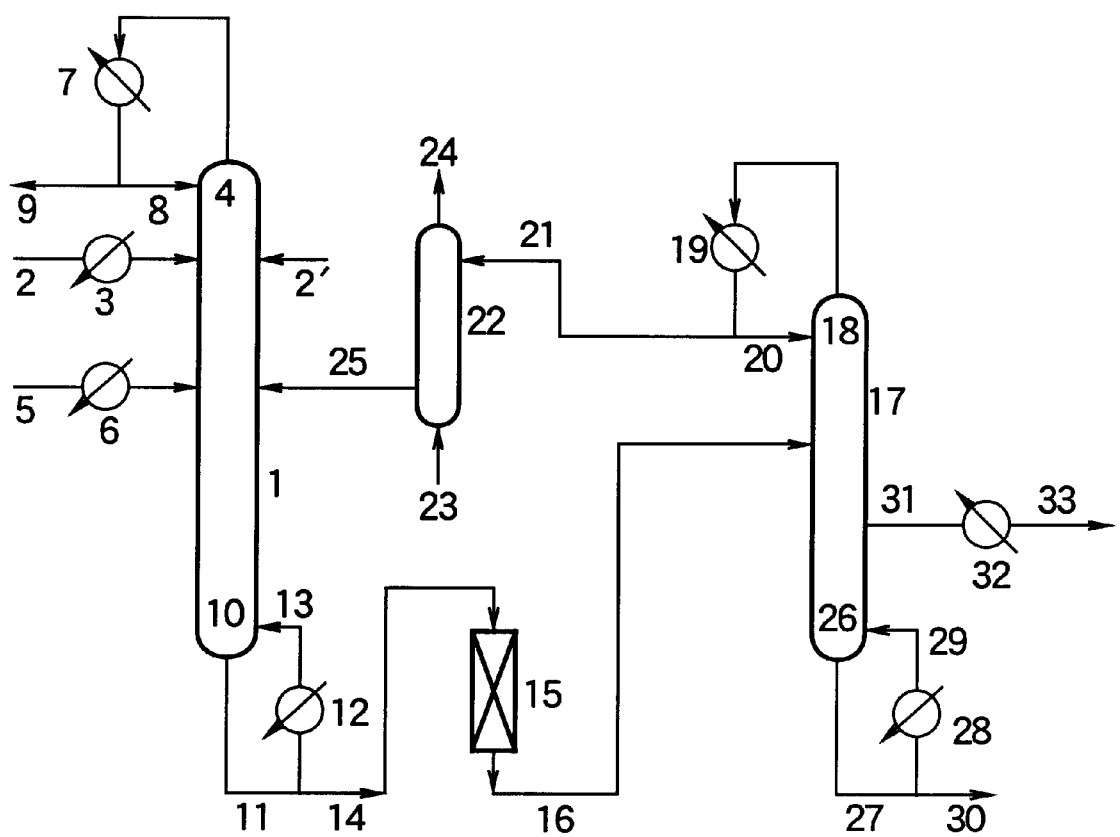
FIG. 1 is a diagram showing the system which was used for practicing Example 1 of the present application.

1 continuous multi-stage distillation column
3, 6 preheater
4, 18, 42, 61 top of column
7, 19, 32, 45, 62 condenser
10, 26, 43, 65 bottom of column
12, 28, 50, 67 reboiler
15, 34 continuous etherification reactor
72 hydrolysis reactor
17 low boiling point mixture separation column or low boiling point mixture separation/etherification column
22, 38 carbon dioxide separation column
41 diol (ethylene glycol) purification column
60 water separation column
2, 2', 5, 8, 9, 11, 13, 14, 16, 20, 21, 23, 24, 25, 27, 29, 30, 31, 33, 35, 36, 37, 39, 46, 47, 48, 49, 51, 52, 56, 63, 64, 66, 68, 69, 70, 71 conduit

DETAILED DESCRIPTION OF THE INVENTION

According to the present invention, there is provided a method for continuously producing a dialkyl carbonate and a diol from a cyclic carbonate and an aliphatic monohydric alcohol, comprising:

(1) continuously feeding a cyclic carbonate represented by the following formula (A):

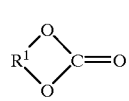

(A)

wherein $R^1$ is a divalent group which is represented by the formula $—(CH_2)_m—$, wherein m is an integer of from 2 to 6, and which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

For an easy understanding of the present invention, the essential features and various preferred embodiments of the present invention are enumerated below.

1. A method for continuously producing a dialkyl carbonate and a diol from a cyclic carbonate and an aliphatic monohydric alcohol, comprising:

(1) continuously feeding a cyclic carbonate represented by the following formula (A):

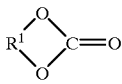
(A)

wherein $R^1$ is a divalent group which is represented by the formula $-(CH_2)_m-$, wherein m is an integer of from 2 to 6, and which is unsubstituted or substituted with at least one substituent selected from the group consisting of a $C_1-C_{10}$ alkyl group and a $C_6-C_{10}$ aryl group, and an aliphatic monohydric alcohol represented by the following formula (B):

$R^2OH$ (B)

wherein $R^2$ is a monovalent aliphatic $C_1-C_{12}$ hydrocarbon group which is unsubstituted or substituted with at least one substituent selected from the group consisting of a $C_1-C_{10}$ alkyl group and a $C_6-C_{10}$ aryl group, to a continuous multi-stage distillation column, and continuously effecting a transesterification between the cyclic carbonate and the aliphatic monohydric alcohol in the presence of a transesterification catalyst in the multi-stage distillation column, thereby continuously producing a dialkyl carbonate represented by the following formula (C):

(C)

wherein $R^2$ is as defined for formula (B) above, and a diol represented by the following formula (D):

(D)

wherein $R^1$ is as defined for formula (A) above, while continuously withdrawing a low boiling point mixture in a gaseous form containing the produced dialkyl carbonate (C) and the unreacted aliphatic monohydric alcohol (B) from an upper portion of the multi-stage distillation column and continuously withdrawing a high boiling point mixture in a liquid form containing the produced diol (D) and the unreacted cyclic carbonate (A) from a lower portion of the multi-stage distillation column, and (2) continuously feeding the high boiling point mixture withdrawn from the lower portion of the multi-stage distillation column in step (1) to a continuous etherification reactor, to thereby effect a continuous etherification reaction between the unreacted cyclic carbonate (A) and a part of the produced diol (D) and produce a chain ether represented by the following formula (E):

$HO(R^1O)_pH$ (E)

wherein $R^1$ is as defined for formula (A) above and p is an integer of from 2 to 4, and carbon dioxide, while continuously withdrawing the resultant etherification reaction mixture containing the remainder of the diol (D) produced in step (1) and the produced chain ether (E) from the continuous etherification reactor, the etherification reaction mixture having a cyclic carbonate content of from 0 to $10^{-2}$ in terms of the weight ratio of the cyclic carbonate (A) to the diol (D).

the etherification reaction mixture having a cyclic carbonate content of from 0 to $10^{-2}$ in terms of the weight ratio of the cyclic carbonate (A) to the diol (D).

2. The method according to item 1 above, wherein the conversion of the cyclic carbonate in the transesterification in step (1) is 50% or more.

3. The method according to item 2 above, wherein the conversion of the cyclic carbonate in the transesterification in step (1) is from 95 to 99.999%.

4. The method according to any one of items 1 to 3 above, wherein, in step (2), the continuous etherification reaction is conducted in the presence of an etherification catalyst.

5. The method according to any one of items 1 to 4 above, wherein the conversion of the cyclic carbonate in the continuous etherification reaction in step (2) is from 90 to 100%

6. The method according to any one of items 1 to 5 above, wherein the etherification reaction mixture withdrawn from the continuous etherification reactor in step (2) contains the carbon dioxide, and wherein the carbon dioxide is removed from the etherification reaction mixture.

7. The method according to any one of items 1 to 6 above, wherein the aliphatic monohydric alcohol used in step (1) contains a concomitant dialkyl carbonate in an amount of from 0 to 40% by weight, based on the total weight of the aliphatic monohydric alcohol and the concomitant dialkyl carbonate.

8. The method according to any one of items 1 to 7 above, wherein the high boiling point mixture withdrawn from the lower portion of the continuous multi-stage distillation column in step (1) contains a part of the unreacted aliphatic monohydric alcohol, and wherein the high boiling point mixture is continuously introduced, prior to the feeding thereof to the continuous etherification reactor in step (2), to a low boiling point mixture separation column which is comprised of a continuous multi-stage distillation column, and wherein a low boiling point mixture containing the part of the unreacted aliphatic monohydric alcohol which is contained in the high boiling point mixture is continuously withdrawn from an upper portion of the low boiling point mixture separation column, while continuously withdrawing a high boiling point mixture containing the diol (D) and the unreacted cyclic carbonate (A) from the low boiling point mixture separation column through one or more side-cut withdrawal ports provided in a side wall of the column at one or more positions thereof corresponding to one or more stages selected from the group consisting of intermediate stages and a lowermost stage of the low boiling point mixture separation column, wherein the low boiling point mixture withdrawn from the upper portion of the low boiling point mixture separation column is continuously recycled to the multi-stage distillation column used in step (1), while continuously feeding the high boiling point mixture withdrawn through the side-cut withdrawal port of the low boiling point mixture separation column to the continuous etherification reactor used in step (2).

9. The method according to any one of items 1 to 7 above, wherein the high boiling point mixture withdrawn from the lower portion of the continuous multi-stage distillation column in step (1) contains a part of the unreacted aliphatic monohydric alcohol, and wherein the high boiling point mixture is continuously introduced, prior to the feeding thereof to the continuous etherification reactor in step (2), to a low boiling point mixture separation column which is comprised of a continuous multi-stage distillation column, and wherein a low boiling point mixture containing the part of the unreacted aliphatic monohydric alcohol which is contained in the high boiling point mixture is continuously withdrawn from an upper portion of the low boiling point mixture separation column, while continuously withdrawing a high boiling point mixture containing the diol (D) and the unreacted cyclic carbonate (A) from a lower portion of the low boiling point mixture separation column, wherein the low boiling point mixture withdrawn from the upper portion of the low boiling point mixture separation column is continuously recycled to the multi-stage distillation column used in step (1), while continuously feeding the high boiling point mixture withdrawn from the lower portion of the low boiling point mixture separation column to the continuous etherification reactor used in step (2).

10. The method according to any one of items 1 to 7 above, wherein the high boiling point mixture withdrawn from the lower portion of the continuous multi-stage distillation column in step (1) contains a part of the unreacted aliphatic monohydric alcohol, and wherein the high boiling point mixture is continuously introduced to a low boiling point mixture separation/etherification column which is comprised of a continuous multi-stage distillation column having a lower portion thereof of adapted for serving as the continuous etherification reactor used in step (2), and wherein the continuous etherification reaction between the unreacted cyclic carbonate (A) and the diol (D) is effected in the lower portion of the low boiling point mixture separation/etherification column to produce the chain ether (E) and the carbon dioxide, while continuously withdrawing a low boiling point mixture containing the carbon dioxide and containing the part of the unreacted aliphatic monohydric alcohol which is contained in the high boiling point mixture from an upper portion of the low boiling point mixture separation/etherification column and continuously withdrawing a high boiling point mixture comprising the etherification reaction mixture containing the remainder of the diol (D) produced in step (1) and the produced chain ether (E) from the lower portion of the low boiling point mixture separation/etherification column, wherein the low boiling point mixture withdrawn from the upper portion of the low boiling point mixture separation/etherification column is continuously recycled to the multi-stage distillation column used in step (1).

11. The method according to any one of items 1 to 10 above, wherein the cyclic carbonate is ethylene carbonate and the aliphatic monohydric alcohol is selected from the group consisting of methanol, ethanol, n-propanol, iso-propanol, n-butanol, iso-butanol, sec-butanol and tert-butanol.

12. The method according to any one of items 1 to 11 above, wherein the cyclic carbonate is ethylene carbonate, the aliphatic monohydric alcohol is methanol and the chain ether is diethylene glycol.

Hereinbelow, the present invention will be explained in detail.

The reaction performed in the present invention is a reversible, equilibrium transesterification reaction represented by the following reaction scheme (I), in which a dialkyl carbonate (C) and a diol (D) are produced from a cyclic carbonate (A) and an aliphatic monohydric alcohol (B):

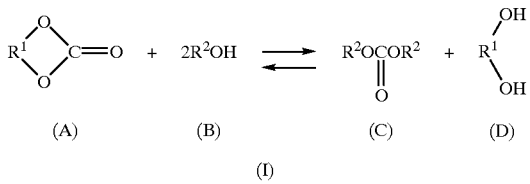

wherein:

R$^1$ is a divalent group which is represented by the formula —(CH$_2$)$_m$—, wherein m is an integer of from 2 to 6, and which is unsubstituted or substituted with at least one substituent selected from the group consisting of a C$_1$–C$_{10}$ alkyl group and a C$_6$–C$_{10}$ aryl group, and R$^2$ is a monovalent aliphatic C$_1$–C$_{12}$ hydrocarbon group which is unsubstituted or substituted with at least one substituent selected from the group consisting of a C$_1$–C$_{10}$ alkyl group and a C$_6$–C$_{10}$ aryl group.

As mentioned above, the reaction performed in the present invention is a reversible, equilibrium reaction. Therefore, even when it is possible to achieve a substantially 100% conversion of a cyclic carbonate, it is impossible to prevent a trace amount of the cyclic carbonate from remaining unreacted in a produced diol. Further, for separating a high purity diol from a mixture of a cyclic carbonate and a diol, it is necessary to perform a distillation separation of the high purity diol under strictly controlled conditions.

In the method of the present invention, the unreacted cyclic carbonate remaining in the produced diol is converted into an ether, which can be easily separated from the diol. Therefore, in the present invention, a high purity diol can be easily obtained without a need for the above-mentioned distillation separation to be performed under strictly controlled conditions.

As mentioned above, there is known a method for obtaining a high purity diol, in which the unreacted cyclic carbonate is hydrolyzed to form a diol (WO 97/23445 (corresponding to U.S. Pat. No. 5,847,189 and EP 0889025)). Differing from the method of WO 97/23445, the method of the present invention enables a high purity diol to be easily obtained by a simple process which does not require the use of water and hence does not require cumbersome operations (such as water removal operation) caused by the use of water. Therefore, the method of the present invention is very advantageous, as compared to the method of the above-mentioned WO 97/23445.

In step (2) of the method of the present invention, the etherification reaction is effected to the extent that the etherification reaction mixture withdrawn from the continuous etherification reactor has a cyclic carbonate content of from 0 to 10$^{-2}$ in terms of the weight ratio of the cyclic carbonate to the diol. Conventionally, such an etherification reaction, in which an unreacted cyclic carbonate which can be recycled to the transesterification reaction system is consumed, has been considered as undesired. Therefore, in the prior art, operations for separating a diol from a mixture of a diol and a cyclic carbonate have been performed under conditions which do not cause such an etherification reaction.

In Comparative Examples 1 and 2 of the above-mentioned WO 97/23445, instead of hydrolyzing an unreacted cyclic carbonate remaining in a diol, a step for separating the diol from the unreacted cyclic carbonate is performed. In the separation step performed in Comparative Examples 1 and 2 of WO 97/23445, a part of the unreacted cyclic carbonate (unreacted ethylene carbonate) happens to be converted into ethers (diethylene glycol and triethylene glycol). However, since this conversion of unreacted ethylene carbonate into ethers is not intentional, the diol (ethylene glycol) obtained by this separation step contains a large amount of unreacted ethylene carbonate (specifically, the ethylene carbonate/ethylene glycol weight ratios in Comparative Examples 1 and 2 of WO 97/23445 are 40.3/59.7 and 13.5/86.5, respectively).

Thus, there have conventionally been no attempt to obtain a high purity diol by a method in which almost all or all of an unreacted cyclic carbonate remaining in a produced diol is converted into an ether. It is quite unexpected that a high purity diol can be easily obtained by the method of the present invention in which the etherification reaction is performed to the extent that the etherification reaction mixture withdrawn from the continuous etherification reactor in step (2) has a cyclic carbonate content of from 0 to 10$^{-2}$ in terms of the weight ratio of the cyclic carbonate to the diol.

With respect to the continuous multi-stage distillation column to be used in step (1) of the method of the present invention, there is no particular limitation, as long as it is a distillation column which has two or more stages of distillation and which is capable of continuous distillation. In the present invention, the term "stages" is intended to include theoretical stages (theoretical plates). In the case of a distillation column having no substantive stages, such as a packed column, the value obtained by dividing the packing height by the height per theoretical stage (plate) (H.E.T.P.) (height equivalent to a theoretical plate) is considered as the number of stages. Examples of such continuous multi-stage distillation columns include plate type columns using a tray, such as a bubble-cap tray, a sieve tray, a valve tray, a counterflow tray, and packed type columns packed with various packings, such as a Raschig ring, a Lessing ring, a Pall ring, a Berl saddle, an Interlox saddle, a Dixon packing, a McMahon packing, a Heli pack, a Sulzer packing and Mellapak. Any column which is generally used as a continuous multi-stage distillation column can be utilized. Further, a mixed type of plate column and packed column, which comprises both a plate portion and a portion packed with packings, can also be preferably used. When a solid catalyst which is insoluble in the liquid phase in a distillation column is used, a packed column type distillation column, in which the solid catalyst is used in substitution for part or all of the packings, is preferably employed. As the continuous multi-stage distillation column to be used in step (1) of the method of the present invention, the above-mentioned distillation columns can be used individually or in combination. When used in combination, a plurality of distillation columns may be connected in series or in parallel.

A cyclic carbonate used as a feedstock in the method of the present invention is represented by formula (A) in reaction scheme (I) mentioned above. Examples of cyclic carbonates include alkylene carbonates, such as ethylene carbonate and propylene carbonate, 1,3-dioxacyclohexa-2-one, 1,3-dioxacyclohepta-2-one, and the like. Of these cyclic carbonates, ethylene carbonate and propylene carbonate are preferred because of their good availability. Ethylene carbonate is most preferred.

An aliphatic monohydric alcohol used as another feedstock in the method of the present invention is a compound which is represented by formula (B) in reaction scheme (I) mentioned above and has a boiling point lower than that of the produced diol. The type of an aliphatic monohydric alcohol which can be used in the method of the present invention varies depending on the type of the cyclic carbonate used. Examples of aliphatic monohydric alcohols include methanol, ethanol, propanol (isomers), allyl alcohol, butanol (isomers), 3-butene-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), diethylcyclohexanol (isomers), phenylcyclohexanol (isomers), benzyl alcohol, phenethyl alcohol (isomers), phenylpropanol (isomers) and the like. The above-mentioned aliphatic monohydric alcohol may be substituted with at least one substituent, such as a halogen atom, a lower alkoxy group, a cyano group, an alkoxycarbonyl group, an aryloxycarbonyl group, an acyloxy group or a nitro group.

Of these aliphatic monohydric alcohols, an alcohol having 1 to 6 carbon atoms is preferred. More preferred are monohydric alcohols having 1 to 4 carbon atoms, i.e., methanol, ethanol, n-propanol, iso-propanol, n-butanol, iso-butanol, sec-butanol and tert-butanol. When ethylene carbonate or propylene carbonate is used as a cyclic carbonate, methanol and ethanol are preferred, and especially preferred is methanol.

In the method of the present invention, the reaction represented by reaction scheme (I) is conducted by the technique of reactive distillation, that is, the reaction is conducted in a continuous multi-stage distillation column while separating a produced low boiling point mixture from the reaction system by distillation.

In the method of the present invention, a transesterification catalyst is placed in the continuous multi-stage distillation column. The method for causing a transesterification catalyst to be present in the multi-stage distillation column is not particularly limited. For example, a homogeneous catalyst which is soluble in the reaction system under the reaction conditions can be caused to be present in the continuous multi-stage distillation column by continuously feeding the homogeneous catalyst to the continuous multi-stage distillation column. Alternatively, a heterogeneous catalyst (solid catalyst) which is insoluble in the reaction system under the reaction conditions, can be caused to be present in the continuous multi-stage distillation column by packing the solid catalyst in the continuous multi-stage distillation column. The abovementioned homogeneous and heterogeneous catalysts can be used in combination.

When a homogeneous catalyst is continuously fed to the continuous multi-stage distillation column, it may be fed to the distillation column together with a feedstock cyclic carbonate and/or a feedstock aliphatic monohydric alcohol. Alternatively, the homogeneous catalyst may be fed to the distillation column at a position different from that at which the feedstock is fed. Further, the homogeneous catalyst can be fed to the distillation column at any position as long as the position is at least one theoretical stage (plate) above the column bottom. However, since the region where the reaction actually takes place in the continuous multi-stage distillation column is generally below the position at which the homogeneous catalyst is fed, it is preferred that the homogeneous catalyst is fed to the distillation column at a position between the top of the column and the position at which the feedstock is fed.

When a heterogeneous solid catalyst is used as a catalyst, the catalyst can be packed in a desired amount at a desired position of the continuous multi-stage distillation column, as long as the catalyst layer present in the column has a height which corresponds to at least one theoretical stage (plate), preferably two or more theoretical stages (plates). A catalyst which can serve as a packing for the continuous multi-stage distillation column can also be used.

As a transesterification catalyst used in the present invention, various types of known catalysts can be used. Examples of such catalysts include alkali metals or alkaline earth metals, such as lithium, sodium, potassium, rubidium, cesium, magnesium, calcium, strontium and barium; basic compounds, such as hydrides, hydroxides, alkoxides, aryloxides and amides of alkali metals or alkaline earth metals; basic compounds, such as carbonates and hydrogencarbonates of alkali metals or alkaline earth metals and alkali metal or alkaline earth metal salts of organic acids; tertiary amines, such as triethylamine, tributylamine, trihexylamine and benzyldiethylamine; nitrogen-containing heteroaromatic compounds, such as N-alkylpyrrole, N-alkylindole, oxazole, N-alkylimidazole, N-alkylpyrazole, oxadiazole, pyridine, alkylpyridine, quinoline, alkylquinoline, isoquinoline, alkylisoquinoline, acridine, alkylacridine, phenanthroline, alkylphenanthroline, pyrimidine, alkylpyrimidine, pyradine, alkylpyradine, triazine and alkyltriazine; cyclic amidines, such as diazabicycloundecene (DBU) and diazabicyclononene (DBN); thallium compounds, such as thallium oxide, thallium halides, thallium hydroxide, thallium carbonate, thallium nitrate, thallium sulfate and thallium salts of organic acids; tin compounds, such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride and tin 2-ethylhexanoate; zinc compounds, such as dimethoxyzinc, diethoxyzinc, ethylenedioxyzinc and dibutoxyzinc; aluminum compounds, such as aluminum trimethoxide, aluminum triisopropoxide and aluminum tributoxide; titanium compounds, such as tetramethoxytitanium, tetraethoxytitanium, tetrabutoxytitanium, dichlorodimethoxytitanium, tetraisopropoxytitanium, titanium acetate and titanium acetylacetonate; phosphorus compounds, such as trimethylphosphine, triethylphosphine, tributylphosphine, triphenylphosphine, tributylmethylphosphonium halides, trioctylbutylphosphonium halides and triphenylmethylphosphonium halides; zirconium compounds, such as zirconium halides, zirconium acetylacetonate, zirconium alkoxides and zirconium acetate; lead and lead-containing compounds, e.g., lead oxides, such as PbO, $PbO_2$ and $Pb_3O_4$; lead sulfides, such as PbS, $Pb_2S_3$ and $PbS_2$; lead hydroxides, such as $Pb(OH)_2$, $Pb_3O_2(OH)_2$, $Pb_2[PbO_2(OH)_2]$ and $Pb_2O(OH)_2$; plumbites, such as $Na_2PbO_2$, $K_2PbO_2$, $NaHPbO_2$ and $KHPbO_2$; plumbates, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3.Pb(OH)_2$; alkoxylead compounds and aryloxylead compounds, such as $Pb(OCH_3)_2$, $(CH_3O)Pb(OPh)$ and $Pb(OPh)_2$; lead salts of organic acids, and carbonates and basic salts thereof, such as $Pb(OCOCH_3)_2$, $Pb(OCOCH_3)_4$ and $Pb(OCOCH_3)_2.PbO.3H_2O$; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_2PbO$ wherein Bu represents a butyl group and Ph represents a phenyl group; lead alloys, such as Pb—Na, Pb—Ca, Pb—Ba, Pb—Sn and Pb—Sb; lead minerals, such as galena and zinc blende; hydrates of these lead compounds; ion-exchangers, such as anion-exchange resins having tertiary amino groups, ion-exchange resins having amide groups, ion-exchange resins having at least one type of ion-exchange group selected from the group consisting of sulfonate, carboxylate and phosphate groups, and strongly basic solid anion-exchangers having quaternary ammonium groups as ion-exchange groups; solid inorganic compounds, such as silica, silica-alumina, silica-magnesia, aluminosilicate, gallium silicate, various types of zeolites, various types of metal-exchanged zeolites and ammonium-exchanged zeolites.

Among the above-mentioned solid catalysts, strongly basic anion-exchangers having quaternary ammonium groups as anion-exchange groups are preferred. Examples of such anion-exchangers include strongly basic anion-exchange resins having quaternary ammonium groups as anion-exchange groups, cellulose type strongly basic anion-exchangers having quaternary ammonium groups as anion-exchange groups and strongly basic anion-exchangers carried on an inorganic carrier which have quaternary ammonium groups as anion-exchange groups.

Of these strongly basic anion-exchange resins having quaternary ammonium groups as ion-exchange groups, styrene type strongly basic anion-exchange resins and the like are preferred. A styrene type strongly basic anion-exchange resin is comprised of a styrene/divinylbenzene copolymer as a base resin, and quaternary ammonium groups (type I or type II) as anion-exchange groups, examples of which are diagrammatically represented by the following formulae (II).

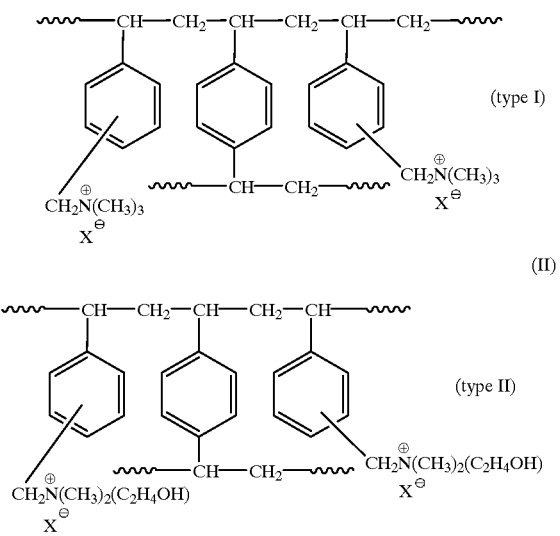

In above formulae (II), X represents an anion. Generally, X is at least one type of anion selected from the group consisting of $F^-$, $Cl^-$, $Br^-$, $I^-$, $HCO_3^-$, $CO_3^{2-}$, $CH3CO_2^-$, $HCO_2^-$, $IO_3^-$, $BrO_3^-$ and $ClO_3^-$. It is preferred that X is selected from the group consisting of $Cl^-$, $Br^-$, $HCO_3^-$ and $CO_3^{2-}$. With respect to the structure of the base resin of the anion-exchange resin, either a gel type or a macroreticular type (MR type) can be used. However, because of the high resistance to organic solvents, the MR type is preferred.

Examples of cellulose type strongly basic anion-exchangers having quaternary ammonium groups as ion-exchange groups include cellulose type strongly basic anion-exchangers having ion-exchange groups of the structure represented by the formula: $—OCH_2CH_2NR_3X$, which exchangers are obtained by trialkylaminoethylation of a part or all of the hydroxyl groups of cellulose. In the above formula, R represents an alkyl group, for example, a methyl group, an ethyl group, a propyl group, a butyl group or the like, preferably a methyl group or an ethyl group; and X is as defined above.

The inorganic carrier-carried strongly basic anion-exchanger usable in the present invention, which has quaternary ammonium groups as ion-exchange groups, is an anion-exchanger having quaternary ammonium groups represented by the formula $—O(CH_2)_nNR_3X$ wherein R and X are as defined above and n is usually an integer of from 1 to 6, preferably 2, which anion-exchanger can be prepared by the modification of a part or all of the hydroxyl groups on the surface of the inorganic carrier. Examples of inorganic carriers include silica, alumina, silica-alumina, titania and zeolite. Of these, silica, alumina and silica-alumina are preferred. Silica is most preferred. There is no limitation with respect to the method for the modification of hydroxyl groups on the surface of the inorganic carrier. For example, such a strongly basic anion-exchanger carried on an inorganic carrier can be obtained by subjecting an inorganic carrier and an aminoalcohol represented by the formula $HO(CH_2)_nNR_2$ to a dehydration reaction between them in the presence of a basic catalyst to thereby effect aminoalkoxylation, followed by the reaction of the resultant aminoalkoxylated inorganic carrier with an alkyl halide represented by the formula RX', wherein X' represents a halogen atom, preferably Cl, Br or I, to thereby convert the aminoalkoxy group into a $—O(CH_2)_nNR_3X'$ group. The $—O(CH_2)_nNR_3X'$ group is further converted to a $—O(CH_2)_n NR_3X$ group having the desired anion X by an anion exchange reaction. When n is 2, an inorganic carrier is treated with N,N-dialkylaziridine so that the hydroxyl groups on the inorganic carrier are N,N-dialkylaminoethoxylated to obtain a $—OCH_2CH_2NR_2$ group, which is then converted to a $—OCH_2CH_2NR_3X$ group by the above-mentioned method.

Commercially available solid, strongly basic anion-exchangers having quaternary ammonium groups as ion-exchange groups can be used in the present invention. When a commercially available solid, strongly basic anion-exchanger is used, it can be treated for anion-exchange with a desired anion species before it is used as a transesterification catalyst.

A solid catalyst comprised of a macroreticular or gel type organic polymer or an inorganic carrier, each having bonded thereto a heterocyclic group containing at least one nitrogen atom, is preferably used as a transesterification catalyst. Further, the abovementioned solid catalyst can be treated for quaternarizing a part or all of the nitrogen-containing heterocyclic groups before it is used.

The amount of the transesterification catalyst to be used in the present invention varies depending on the type thereof. The homogeneous catalyst, which is soluble in the reaction system under the reaction conditions, is fed continuously in an amount of from 0.0001 to 50% by weight, based on the total weight of the feedstock cyclic carbonate and the feedstock aliphatic monohydric alcohol. When the solid catalyst is packed in the continuous multi-stage distillation column, it is packed preferably in an amount of from 0.01 to 75% by volume, based on the internal volume of the empty distillation column.

There is no particular restriction with respect to the method for continuously feeding a cyclic carbonate and an aliphatic monohydric alcohol to the continuous multi-stage distillation column, and any feeding method can be used as long as the feedstocks can be contacted with the catalyst in a region of the distillation column which corresponds to at least one stage, preferably at least two stages. That is, the cyclic carbonate and the aliphatic monohydric alcohol can be continuously fed to one or more stages of the continuous multi-stage distillation column through a desired number of feeding pipes at one or more desired locations as long as the above requirement is satisfied. The cyclic carbonate and the monohydric alcohol may be fed either to the same stage of the distillation column or to separate stages individually. The feedstocks are continuously fed in a liquid form, a gaseous form or a gas-liquid mixture form. In addition to the feeding of the feedstocks to the continuous multi-stage distillation column as described above, additional feedstocks can be fed in a gaseous form to the lower portion of the distillation column intermittently or continuously. Also preferred is a method wherein the cyclic carbonate is continuously fed in a liquid form or a gas-liquid mixture form to a stage at a level higher than the stage where the catalyst is present, while the aliphatic monohydric alcohol is continuously fed to the lower portion of the distillation column in a gaseous form or a gas-liquid mixture form, or in a gaseous form and in a liquid form individually. In this case, some of the aliphatic monohydric alcohol may be contained in the cyclic carbonate.

In the present invention, a small amount of a diol as a desired product may be contained in the feedstocks. Further, the aliphatic monohydric alcohol may contain a concomitant dialkyl carbonate. When the aliphatic monohydric alcohol contains a concomitant dialkyl carbonate, the amount of the concomitant dialkyl carbonate in the aliphatic monohydric alcohol is generally in the range of from 0 to 40% by weight, preferably from 0.1 to 30% by weight, more preferably from 1 to 20% by weight, based on the total weight of the aliphatic monohydric alcohol and the concomitant dialkyl carbonate.

In step (1), the ratio of the aliphatic monohydric alcohol to the cyclic carbonate to be fed to the continuous multi-stage distillation column may vary depending on the type and quantity of the transesterification catalyst and the reaction conditions, but, in general, the molar ratio of the aliphatic monohydric alcohol to the cyclic carbonate may be in the range of from 0.01 to 1,000. For increasing the conversion of the cyclic carbonate, it is preferred to feed the aliphatic monohydric alcohol in an excess amount which is 2 times or more by mole the mole of the cyclic carbonate. However, too high a concentration of the aliphatic monohydric alcohol is undesirable because the size of the reaction equipment needs to be large. Therefore, it is especially preferred to use the aliphatic monohydric alcohol in an amount which is 2 to 20 times by mole the mole of the cyclic carbonate.

When carbon dioxide is present in a high concentration in the transesterification reaction system in step (1) of the method of the present invention, the reaction rate becomes low. Therefore, the $CO_2$ concentration of the reaction system is generally not higher than 500 ppm by weight, preferably not higher than 200 ppm by weight, more preferably not higher than 100 ppm by weight.

Also when water is present in a high concentration in the transesterification reaction system in step (1) of the method of the present invention, hydrolysis takes place simultaneously with the transesterification, resulting in a decrease in the selectivity for dialkyl carbonate in step (1). Therefore, the water concentration of the reaction system is generally not higher than 200 ppm by weight, preferably not higher than 100 ppm by weight.

In the method of the present invention, when it is attempted to render the conversion of the cyclic carbonate in step (1) close to 100%, the reaction time needs to be prolonged, and the aliphatic monohydric alcohol needs to be used in large excess. On the other hand, when the conversion of the cyclic carbonate is too low, the size of the continuous etherification reactor used in step (2) needs to be large. Therefore, in step (1), the conversion of the cyclic carbonate is generally in the range of from 50% or more, preferably from 95 to 99.999%, more preferably from 98 to 99.99%, most preferably from 99 to 99.99%.

In step (1), the low boiling point mixture in a gaseous form containing the produced dialkyl carbonate and the unreacted aliphatic monohydric alcohol is continuously withdrawn from the upper portion of the continuous multi-stage distillation column. Further, the withdrawn gaseous mixture may also contain a high boiling point product in a small amount.

A withdrawal port of the continuous multi-stage distillation column of step (1) for withdrawing the gaseous low boiling point mixture containing the produced dialkyl carbonate and the unreacted aliphatic monohydric alcohol is preferably provided at a position between the position from which the feedstocks are fed and the top of the distillation column, or in the top of the distillation column. It is more preferred to provide the withdrawal port for the low boiling point mixture in the top of the distillation column. A part of the low boiling point mixture withdrawn from the withdrawal port may be returned to the upper portion of the distillation column to thereby effect the so-called reflux operation. When the reflux ratio is increased by conducting this reflux operation, the distillation efficiency of a low boiling product into a vapor phase is increased, thereby advantageously increasing the concentration of a low boiling point product in the withdrawn gaseous component. However, too much of an increase in the reflux ratio disadvantageously leads to an increase in the thermal energy required. Thus, the reflux ratio is generally chosen in the range of from 0 to 10, preferably from 0 to 5, more preferably from 0 to 3.

By continuously feeding the low boiling point mixture withdrawn from the upper portion of the distillation column in step (1), containing the produced dialkyl carbonate and the unreacted aliphatic monohydric alcohol, to a dialkyl carbonate separation apparatus and continuously recovering the dialkyl carbonate from the separation apparatus, the dialkyl carbonate can be obtained. Examples of such dialkyl carbonate separation apparatuses include a distillation type separation apparatus, an extractive distillation type separation apparatus, a liquid-liquid extraction type separation apparatus, a crystallization type separation apparatus, an adsorption type separation apparatus and a membrane type separation apparatus. A combination of a plurality of different or identical separation apparatuses may be used. Among these separation apparatuses, a distillation type separation apparatus is especially preferred.

When the low boiling point mixture (containing the produced dialkyl carbonate and the unreacted aliphatic monohydric alcohol) withdrawn from the upper portion of the multi-stage distillation column in step (1) is subjected to separation by means of a distillation type separation apparatus, the low boiling point mixture can be separated into various components, such as the unreacted aliphatic monohydric alcohol and the produced dialkyl carbonate, wherein some of the separated components are obtained in the form of one or more column top fractions containing a single component or a plurality of components and some of the separated components are obtained in the form of a column bottom liquid. As the above-mentioned column top fraction, an azeotropic mixture may be obtained depending on the types of feedstocks. After the components in the low boiling point mixture withdrawn from the upper portion of the multi-stage distillation column in step (1) are separated by means of a distillation type separation apparatus, one or more fractions containing the unreacted aliphatic monohydric alcohol and/or a column bottom liquid containing the unreacted aliphatic monohydric alcohol is then fed to the continuous multi-stage distillation column used in step (1).

As the distillation type separation apparatus, a single continuous multi-stage distillation column or a plurality of continuous multi-stage distillation columns can be used, wherein each continuous multi-stage distillation column may be of the same type as used in step (1). Explained hereinbelow is a mode of the method of the present invention in which an aliphatic monohydric alcohol and a dialkyl carbonate form a minimum boiling point azeotropic mixture, and wherein dimethyl carbonate is produced by using methanol as the aliphatic monohydric alcohol. A low boiling point mixture (containing methanol and dimethyl carbonate) withdrawn from the upper portion of the continuous multi-stage distillation column used in step (1) is continuously fed to a dimethyl carbonate separation column. A low boiling point mixture containing a minimum boiling point azeotropic mixture of methanol and dimethyl carbonate is continuously withdrawn from an upper portion of the dimethyl carbonate separation column, while continuously withdrawing dimethyl carbonate from a lower portion of the dimethyl carbonate separation column, thereby obtaining dimethyl carbonate. As the dimethyl carbonate separation column, a single continuous multistage distillation column or a plurality of continuous multi-stage distillation columns can be used, wherein each continuous multi-stage distillation column may be of the same type as used in step (1). The dimethyl carbonate separation column is generally operated under reduced pressure, atmospheric pressure ($1.013 \times 10^5$ Pa, i.e., 1.033 kg/cm$^2$) or superatmospheric pressure, specifically in the range of from $0.5 \times 10^5$ to $50 \times 10^5$ Pa (0.51 to 51 kg/cm$^2$) in terms of the absolute pressure. The composition of methanol/dimethyl carbonate minimum boiling point azeotropic mixture may be varied depending on the operating pressure of the dimethyl carbonate separation column. Therefore, the operating pressure of the dimethyl carbonate separation column is chosen so that the dimethyl carbonate is obtained from the lower portion of the dimethyl carbonate separation column. Specifically, an operating pressure higher than an operating pressure corresponding to the methanol/dimethyl carbonate ratio of the low boiling point mixture withdrawn from the upper portion of the column of step (1) is chosen for the dimethyl carbonate separation column.

The low boiling point mixture (containing a minimum boiling point azeotropic mixture) withdrawn from the upper portion of the above-mentioned dimethyl carbonate separation column may be fed to the continuous multi-stage distillation column used in step (1) as a feedstock usable in the present invention, i.e., methanol containing dimethyl carbonate.

A diol produced in step (1) of the method of the present invention is continuously withdrawn from a lower portion of the continuous multi-stage distillation column used in step (1) in a liquid form.

In the method of the present invention, the upper portion of the continuous multi-stage distillation column means a portion between the top of the distillation column and a position at approximately half the height of the distillation column, and the upper portion includes the top of the column. The lower portion of the continuous multi-stage distillation column means a portion between the bottom of the distillation column and a position at approximately half the height of the distillation column, and the lower portion includes the bottom of the column.

Further, in the method of the present invention, the liquid mixture withdrawn from the lower portion of the distillation column used in step (1) means a high boiling point mixture continuously withdrawn from the lower portion of the continuous multi-stage distillation column used in step (1), wherein the high boiling point mixture contains the produced diol and the unreacted cyclic carbonate, and may also contain a part of the unreacted aliphatic monohydric alcohol or both a part of the unreacted aliphatic monohydric alcohol and a part of the produced dialkyl carbonate.

When the cyclic carbonate/diol ratio of the liquid mixture withdrawn from the lower portion of the distillation column used in step (1) is too large, the size of the continuous etherification reactor used in step (2) needs to be disadvantageously large. However, for decreasing the cyclic carbonate/diol ratio of the liquid mixture withdrawn from the lower portion of the distillation column used in step (1) to an extremely low level, the conversion of the cyclic carbonate needs to be very close to 100%, which requires that the size of the reaction equipment and the amount of the aliphatic monohydric alcohol be increased. The cyclic carbonate/diol ratio of the liquid mixture withdrawn from the lower portion of the distillation column used in step (1) may be varied depending on the conversion of the cyclic carbonate and the amount of the diol in the feedstocks. However, the weight ratio of the cyclic carbonate to the diol contained in the liquid mixture withdrawn from the lower portion of the distillation column used in step (1) is generally in the range of from $1 \times 10^{-5}$ to $8 \times 10^{-2}$, preferably from $1 \times 10^{-4}$ to $3 \times 10^{-2}$, more preferably from $1 \times 10^{-4}$ to $1 \times 10^{-2}$.

The withdrawal port for withdrawing the liquid mixture containing the produced diol from the continuous multi-stage distillation column used in step (1) is positioned at a lower portion of the distillation column, preferably at the bottom of the distillation column. A part of the withdrawn liquid mixture may be recycled to the lower portion of the continuous multi-stage distillation column in a gaseous form or a gas-liquid mixture form by heating by means of a reboiler.

The rate at which a liquid flows down inside the continuous multi-stage distillation column and the rate at which a vapor ascends inside the distillation column may be varied depending on the type of the distillation column, and on the type of the packing in the case of a packed column. However, the distillation column is generally operated so that no flooding or weeping occurs.

The amount of the dialkyl carbonate produced in the continuous multi-stage distillation column used in step (1) depends on the amount of hold-up liquid in the distillation column. That is, when the height and diameter of a distillation column are not changed, a greater hold-up capacity is preferred because the greater the hold-up capacity, the longer the residence time of the liquid phase, namely, the time during which the reaction is effected. However, when the amount of the hold-up liquid is too large, the residence time becomes too long, so that side reactions and flooding are likely to occur. Accordingly, in step (1) of the method of the present invention, the amount of the hold-up liquid of the continuous multi-stage distillation column varies depending on the distillation conditions and the type of the distillation column. Generally, however, the amount of the hold-up liquid is in the range of from 0.005 to 0.75 in terms of the volume ratio of the hold-up liquid to the empty continuous multi-stage distillation column.

In step (1) of the method of the present invention, the average residence time of the liquid phase in the continuous multi-stage distillation column depends on the reaction conditions, and the type and inner structure (for example, the types of the plate and packing) of the continuous multi-stage distillation column, but is generally in the range of from 0.001 to 50 hours, preferably from 0.01 to 10 hours, more preferably from 0.05 to 5 hours.

The reaction temperature of the transesterification reaction in step (1) means the temperature of the stage of the continuous multi-stage distillation column where the catalyst is present. The reaction temperature varies depending on the types of the feedstocks and the reaction pressure, but is generally chosen in the range of from −20 to 350° C., preferably from 0 to 200° C.

The reaction pressure in the continuous multi-stage distillation column used in step (1) can be selected from reduced pressure, atmospheric pressure and superatmospheric pressure. The reaction pressure is generally in the range of from 1 Pa to $2 \times 10^6$ Pa, ($1.02 \times 10^{-5}$ to 20.4 kg/cm$^2$) preferably from $1 \times 10^3$ Pa to $1 \times 10^6$ Pa, more preferably from $1 \times 10^4$ Pa to $5 \times 10^5$ Pa, in terms of the absolute pressure.

In step (1), it is also possible to supply a part of the high boiling point mixture withdrawn in a liquid form from the lower portion of the multi-stage distillation column to the multi-stage distillation column, so that a part of the unreacted cyclic carbonate and/or a part of the unreacted aliphatic monohydric alcohol can be recycled to the multi-stage distillation column. When a part of the high boiling point mixture withdrawn in a liquid form from the lower portion of the multi-stage distillation column is recycled to the multi-stage distillation column, there is no particular limitation with respect to the position of an introduction port in the multi-stage distillation column, through which the part of the withdrawn high boiling point mixture is supplied to the multi-stage distillation column. However, it is preferred that this introduction port is positioned at an upper portion of the multi-stage distillation column.

With respect to step (2), the high boiling point mixture withdrawn from the lower portion of the multi-stage distillation column in step (1), as such, may be fed to a continuous etherification reactor. Alternatively, using a separation apparatus, from the high boiling point mixture withdrawn from the lower portion of the multi-stage distillation column in step (1), a specific, single component can be separated or a plurality of components can be obtained individually or in mixture, and the component containing a diol and an unreacted cyclic carbonate is then fed to a continuous etherification reactor. As the separation apparatus for effecting the separation of the components in the high boiling point mixture withdrawn from the lower portion of the multi-stage distillation column in step (1), various separation apparatuses, such as a distillation type separation apparatus, an azeotropic distillation type separation apparatus, an extractive distillation type separation apparatus, a liquid-liquid extraction type separation apparatus, a crystallization type separation apparatus, an adsorption type separation apparatus and a membrane type separation apparatus can be used. A combination of a plurality of different or identical separation apparatuses may be used. Among these separation apparatuses, a distillation type separation apparatus is especially preferred.

When the high boiling point mixture (containing the produced diol and the unreacted cyclic carbonate) withdrawn from the lower portion of the multi-stage distillation column in step (1) is subjected to separation by means of a distillation type separation apparatus, the high boiling point mixture can be separated into various components, such as the unreacted cyclic carbonate and the produced diol, wherein some of the components are obtained in the form of one or more column top fractions containing a single component or a mixture of a plurality of components and some of the components are obtained in the form of a column bottom liquid. An azeotropic mixture may occasionally be obtained as the above-mentioned column top fraction, depending on the types of feedstock compounds. After the components in the high boiling point mixture withdrawn from the lower portion of the multi-stage distillation column in step (1) are separated by means of a distillation type separation apparatus, one or more fractions containing the produced diol and the unreacted cyclic carbonate, and/or a column bottom liquid containing the produced diol and the unreacted cyclic carbonate, are then fed to a continuous etherification reactor. As the distillation type separation apparatus, a single continuous multi-stage distillation column or a plurality of continuous multi-stage distillation columns can be used, wherein each continuous multi-stage distillation column may be of the same type as used in step (1).

When a transesterification catalyst soluble in the liquid reaction system under reaction conditions is used, a fraction containing the transesterification catalyst and/or a column bottom liquid containing the transesterification catalyst is obtained. A part or all of the fraction containing the transesterification catalyst and/or the column bottom liquid containing the transesterification catalyst may be recycled to the continuous multi-stage distillation column used in step (1).

Specifically, as preferred examples of manners in which the high boiling point mixture withdrawn from the multi-stage distillation column in step (1) is first subjected to separation by means of a distillation type separation apparatus and then step (2) is conducted by using a continuous etherification reactor, the following two modes can be mentioned.

1. A mode in which the high boiling point mixture withdrawn from the lower portion of the continuous multi-stage distillation column in step (1) contains a part of the unreacted aliphatic monohydric alcohol, and wherein the high boiling point mixture is continuously introduced, prior to the feeding thereof to the continuous etherification reactor in step (2), to a low boiling point mixture separation column which is comprised of a continuous multi-stage distillation column, and wherein a low boiling point mixture containing the part of the unreacted aliphatic monohydric alcohol which is contained in the high boiling point mixture is continuously withdrawn from an upper portion of the low boiling point mixture separation column, while continuously withdrawing a high boiling point mixture containing the diol (D) and the unreacted cyclic carbonate (A) from the low boiling point mixture separation column through one or more side-cut withdrawal ports provided in a side wall of the column at one or more positions thereof corresponding to one or more stages selected from the group consisting of intermediate stages and a lowermost stage of the low boiling point mixture separation column, wherein the low boiling point mixture withdrawn from the upper portion of the low boiling point mixture separation column is continuously recycled to the multi-stage distillation column used in step (1), while continuously feeding the high boiling point mixture withdrawn through the side-cut withdrawal port of the low boiling point mixture separation column to the continuous etherification reactor used in step (2).

As the low boiling point mixture separation column, a continuous multi-stage distillation column can be used, and the continuous multi-stage distillation column may be of the same type as used in step (1).

2. A mode in which the high boiling point mixture withdrawn from the lower portion of the continuous multi-stage distillation column in step (1) contains a part of the unreacted aliphatic monohydric alcohol, and wherein the high boiling point mixture is continuously introduced, prior to the feeding thereof to the continuous etherification reactor in step (2), to a low boiling point mixture separation column which is comprised of a continuous multi-stage distillation column, and wherein a low boiling point mixture containing the part of the unreacted aliphatic monohydric alcohol which is contained in the high boiling point mixture is continuously withdrawn from an upper portion of the low boiling point mixture separation column, while continuously withdrawing a high boiling point mixture containing the diol (D) and the unreacted cyclic carbonate (A) from a lower portion of the low boiling point mixture separation column, wherein the low boiling point mixture withdrawn from the upper portion of the low boiling point mixture separation column is continuously recycled to the multi-stage distillation column used in step (1), while continuously feeding the high boiling point mixture withdrawn from the lower portion of the low boiling point mixture separation column to the continuous etherification reactor used in step (2).

In step (2) of the method of the present invention, the high boiling point mixture withdrawn from the lower portion of the multi-stage distillation column in step (1) is continuously fed to a continuous etherification reactor, to thereby effect a continuous etherification reaction between the unreacted cyclic carbonate (A) and a part of the produced diol (D) and produce a chain ether represented by the following formula (E):

$$HO(R^1O)_pH \qquad (E)$$

wherein $R^1$ is as defined for formula (A) above and p is an integer of from 2 to 4, and carbon dioxide, while continuously withdrawing the resultant etherification reaction mixture containing the remainder of the diol (D) produced in step (1) and the produced chain ether (E) from the continuous etherification reactor. When the high boiling mixture withdrawn from the lower portion of the multi-stage distillation column in step (1) is first fed to a separation apparatus prior to the feeding thereof to the continuous etherification reactor, a fraction containing the unreacted cyclic carbonate and the produced diol, which fraction is obtained in the separation apparatus, is fed to the continuous etherification reactor.

With respect to the continuous etherification reactor used in step (2), there is no particular limitation as long as it is a reaction apparatus which can be used for performing a continuous etherification reaction between a cyclic carbonate and a diol. Examples of reactors usable as the continuous etherification reactor include a tubular reactor; a vessel reactor; a column reactor, such as a distillation column reactor or a bubble column reactor; and a fluidized-bed reactor. It is preferred to use a tubular reactor, a vessel reactor or a distillation column reactor.

When a distillation column reactor is used as the continuous etherification reactor, the distillation column reactor may be a continuous multi-stage distillation column which is of the same type as used in step (1). When the high boiling point mixture withdrawn from the lower portion of the multi-stage distillation column in step (1) is subjected to separation by means of a distillation type separation apparatus (distillation column), it is preferred that the distillation type separation apparatus is caused to serve also as a distillation column type continuous etherification reactor.

In step (2), an etherification catalyst may be used. With respect to the etherification catalyst used in step (2), there is no particular limitation as long as it is one which can be used for producing an ether by a reaction between a cyclic carbonate and a diol. Examples of etherification catalysts include the same compounds as the above-mentioned examples of transesterification catalysts used in step (1).

When the transesterification catalyst used in step (1) is soluble in the liquid reaction system under reaction conditions and also can serve as an etherification catalyst, there are advantages:

that, when the high boiling point mixture which has been withdrawn from the lower portion of the multi-stage distillation column in step (1) is directly fed to the continuous etherification reactor without being subjected to separation in a separation apparatus, the transesterification catalyst used in step (1), as such, can be used as an etherification catalyst in step (2); and that, when the high boiling point mixture which has been withdrawn from the lower portion of the multi-stage stage distillation column in step (1) is first subjected to separation in a distillation column type separation apparatus prior to the feeding thereof to the continuous etherification reactor, a part or all of a fraction containing the transesterification catalyst used in step (1) and/or a part or all of a column bottom liquid containing the transesterification catalyst used in step (1) (which fraction and/or column bottom liquid is obtained by separation), as such, can be used as an etherification catalyst in step (2).

The amount of the etherification catalyst used in the present invention may be varied depending on the type of the etherification catalyst. However, when the etherification catalyst is continuously fed to the continuous etherification reactor, the amount of the etherification catalyst is generally 0.0001 to 50% by weight, based on the weight of the cyclic carbonate fed to the continuous etherification reactor. When a solid catalyst is used in a manner such that the solid catalyst is disposed in the continuous etherification reactor, it is preferred that the amount of the solid catalyst is from 10 to 75% by volume, based on the internal volume of the continuous etherification reactor.

The reaction conditions for the etherification reaction in the continuous etherification reactor may be varied depending on the presence or absence of an etherification catalyst. When an etherification catalyst is used, the etherification reaction conditions may be varied depending on the type and amount of the etherification catalyst. However, in general, the reaction temperature is from 50 to 350° C., preferably from 80 to 300° C., more preferably from 100 to 250° C. The reaction time may be varied depending on the presence or absence of an etherification catalyst. When an etherification catalyst is used, the reaction time may be varied depending on the type and amount of the etherification catalyst and the reaction temperature. However, in general, the reaction time is from 0.001 to 50 hours, preferably from 0.01 to 10 hours, more preferably from 0.02 to 5 hours, in terms of the average residence time. The reaction pressure may be varied depending on the reaction temperature. However, in general, the reaction pressure is from $1 \times 10^3$ to $2 \times 10^7$ Pa, preferably from $1 \times 10^4$ to $1 \times 10^7$ Pa, in terms of the absolute pressure.

The conversion of the cyclic carbonate in the etherification reaction in step (2) of the method of the present invention is generally from 90 to 100%, preferably from 95 to 100%, more preferably from 98 to 100%. The etherification reaction mixture obtained in step (2) is required to have a cyclic carbonate content of from 0 to $10^{-2}$ in terms of the weight ratio of the cyclic carbonate (A) to the diol (D). The cyclic carbonate content of the etherification reaction mixture obtained in step (2) is preferably from 0 to $6 \times 10^{-4}$, more preferably from 0 to $10^{-5}$ in terms of the weight ratio of the cyclic carbonate (A) to the diol (D).

In step (2), the obtained etherification reaction mixture containing the remainder of the diol (D) produced in step (1) and the produced chain ether (E) is continuously withdrawn from the continuous etherification reactor. By subjecting the etherification reaction mixture to distillation, a high purity diol fraction can be obtained from the etherification reaction mixture. Further, when the etherification reaction mixture contains unreacted components, including the unreacted cyclic carbonate and/or the unreacted aliphatic monohydric alcohol, the etherification reaction mixture may be subjected to distillation to separate these unreacted components from the etherification reaction mixture, and these separated components are then recycled to the continuous multi-stage distillation column used in step (1).

When carbon dioxide produced in step (2) enters the reaction system in step (1), the transesterification reaction in step (1) is adversely affected, so that the reaction rate becomes low. Therefore, when the etherification reaction mixture withdrawn from the continuous etherification reactor contains carbon dioxide, it is preferred that the carbon dioxide is separated from the etherification reaction mixture by means of a carbon dioxide separation apparatus. As a carbon dioxide separation apparatus, a separation apparatus utilizing any principle of separation, such as distillation separation, extraction separation or reaction separation, can be employed.

When the continuous etherification reactor used in step (2) is one selected from the group consisting of a tubular reactor and a vessel reactor, the obtained etherification reaction mixture containing the remainder of the diol produced in step (1), the produced chain ether and the produced carbon dioxide may be introduced to a carbon dioxide separation apparatus, and the resultant, carbon dioxide-free etherification reaction mixture and the removed carbon dioxide can be individually withdrawn from the carbon dioxide separation apparatus. The obtained carbon dioxide-free etherification reaction mixture may be subjected to distillation by means of a diol purification column to thereby obtain a purified diol. As the diol purification column, a continuous multi-stage distillation column can be used, and the continuous multi-stage distillation column may be of the same type as used in step (1).

When the continuous etherification reactor used in step (2) is a continuous etherification column comprised of a distillation column (such as a continuous multi-stage distillation column), a high boiling point mixture comprising the etherification reaction mixture containing the remainder of the diol produced in step (1) and the produced chain ether may be withdrawn from a lower portion of the continuous etherification column, while continuously withdrawing a low boiling point mixture containing the produced carbon dioxide from an upper portion of the continuous etherification column. By subjecting this high boiling point mixture to distillation by means of a diol purification column, a purified diol can be obtained.

Further, when the high boiling point mixture withdrawn from the lower portion of the continuous multi-stage distillation column in step (1) contains a part of the unreacted aliphatic monohydric alcohol, wherein the continuous etherification reactor is a continuous etherification column comprised of a continuous multi-stage distillation column, a low boiling point mixture containing the part of the unreacted aliphatic monohydric alcohol and containing the produced carbon dioxide may be continuously withdrawn from an upper portion of the continuous etherification column and recycled to the continuous multi-stage distillation column used in step (1), while continuously withdrawing a high boiling point mixture comprising the etherification reaction mixture containing the remainder of the diol produced in step (1) and the produced chain ether from a lower portion of the continuous etherification column. By subjecting this high boiling point mixture to distillation by means of a diol purification column, a purified diol can be obtained. It is preferred that the low boiling point mixture withdrawn from the upper portion of the continuous etherification column is fed, prior to being recycled to the continuous multi-stage distillation column used in step (1), to a carbon dioxide separation apparatus to thereby separate the carbon dioxide therefrom.

As mentioned above, when the high boiling point mixture withdrawn from the lower portion of the multi-stage distillation column in step (1) is subjected to separation by means of a distillation type separation apparatus (distillation column), it is preferred that the distillation type separation apparatus is caused to serve also as an etherification reactor. In this case, it is preferred that the distillation type separation apparatus (which is caused to serve also as a continuous etherification reactor) is a continuous multi-stage distillation column. Accordingly, as a preferred embodiment of the method of the present invention, there can be mentioned a mode in which the high boiling point mixture withdrawn from the lower portion of the continuous multi-stage distillation column in step (1) contains a part of the unreacted aliphatic monohydric alcohol, and wherein the high boiling point mixture is continuously introduced to a low boiling point mixture separation/etherification column which is comprised of a continuous multi-stage distillation column having a lower portion thereof adapted for serving as the continuous etherification reactor used in step (2), and wherein the continuous etherification reaction between the unreacted cyclic carbonate (A) and diol (D) is effected in the lower portion of the low boiling point mixture separation/etherification column to produce the chain ether (E) and the carbon dioxide, while continuously withdrawing a low boiling point mixture containing the carbon dioxide and containing the part of the unreacted aliphatic monohydric alcohol which is contained in the high boiling point mixture from an upper portion of the low boiling point mixture separation/etherification column and continuously withdrawing a high boiling point mixture comprising the etherification reaction mixture containing the remainder of the diol (D) produced in step (1) and the produced chain ether (E) from the lower portion of the low boiling point mixture separation/etherification column, wherein the low boiling point mixture withdrawn from the upper portion of the low boiling point mixture separation/etherification column is continuously recycled to the multi-stage distillation column used in step (1).

In this preferred embodiment, with respect to the position of the feeding port for feeding the high boiling point mixture (containing the unreacted cyclic carbonate) withdrawn from the lower portion of the continuous multi-stage distillation column used in step (1) to the low boiling point mixture separation/etherification column, there is no particular limitation. However, from the viewpoint of ease in separation of the part of the aliphatic monohydric alcohol (which is a low boiling point product contained in the high boiling point mixture) from the high boiling point mixture, it is preferred that the high boiling point mixture is fed to the low boiling point mixture separation/etherification column at a position above a withdrawal port provided in a side wall of the low boiling point mixture separation/etherification column for withdrawing the etherification reaction mixture containing the remainder of the diol produced in step (1) and the produced chain ether.

In the method of the present invention, it is not necessary to use a solvent. However, for the purposes of, e.g., (1) facilitating the reaction operation and (2) separating a dialkyl carbonate and a diol efficiently by performing azeotropic distillation or extractive distillation, an appropriate inert solvent may be used as a reaction solvent. Examples of inert solvents include an ether, an aliphatic hydrocarbon, an aromatic hydrocarbon, a halogenated aliphatic hydrocarbon and a halogenated aromatic hydrocarbon.

An inert gas, such as nitrogen, helium, argon or the like, may be present in the reaction system. Further, for the purpose of promoting the distilling-off of a generated low boiling point reaction product, the above-mentioned inert gas or a gaseous form of an inert low boiling point organic compound may be introduced to the reaction system from a lower portion of a continuous multi-stage distillation column.

BEST MODE FOR CARRYING OUT THE INVENTION

The present invention will be described in more detail with reference to the following Examples and Comparative Examples, which should not be construed as limiting the scope of the present invention.

In the following Examples and Comparative Examples, the yield (%) of ethylene glycol is determined, based on the amount of the charged ethylene carbonate; the yield (%) of dimethyl carbonate is determined, based on the amount of the charged ethylene carbonate; and the selectivity (%) for dimethyl carbonate is determined, based on the amount of the consumed ethylene carbonate in the transesterification reaction in step (1). The positions of respective stages of a distillation column are represented by the ordinal numbers for the respective stages as counted from the top stage of the distillation column.

In the following Examples and Comparative Examples, the meanings of the following abbreviations are as shown below:

EC: ethylene carbonate,
MeOH: methanol,
DMC: dimethyl carbonate,
EG: ethylene glycol, and
DEG: diethylene glycol.

EXAMPLE 1

Using a production system as shown in FIG. 1, dimethyl carbonate (DMC) and ethylene glycol (EG) were continuously produced from ethylene carbonate (EC) and methanol (MeOH).

Continuous multi-stage distillation column 1 was comprised of a 60-stage Oldershaw distillation column which has an inner diameter of 5 cm. EC was continuously fed in a liquid form to distillation column 1 at the fifth stage thereof through conduit 2 and preheater 3 at a flow rate of 231 g/h, and an 18 wt. % solution of potassium hydroxide (as a catalyst) in ethylene glycol was also continuously fed in a liquid form to distillation column 1 at the fifth stage thereof through conduit 2' at a flow rate of 1.1 g/h, while continuously feeding a mixture of MeOH and DMC (MeOH/DMC weight ratio=95/5) in a liquid form to distillation column 1 at the 30th stage thereof through conduit 5 and preheater 6 at a flow rate of 783.2 g/h, to thereby effect a transesterification reaction. Continuous multi-stage distillation column 1 was operated under conditions wherein the reaction pressure and reaction temperature, each as measured at column top 4 thereof, were atmospheric pressure and 63.8° C., respectively.

A low boiling point mixture in a gaseous form distilled from column top 4 of distillation column 1 was condensed by condenser 7. A part of the resultant condensate was refluxed to column top 4 of distillation column 1 through conduit 8 (reflux ratio: 0.5), while withdrawing the remainder of the condensate from the production system through conduit 9 at a flow rate of 851.3 g/h (hereinbelow, the withdrawn condensate is referred to simply as "column top condensate from column 1"), wherein the column top condensate from column 1 contained MeOH and DMC in concentrations of 67.7% by weight and 32.3% by weight, respectively. On the other hand, a liquid was withdrawn from column bottom 10 of distillation column 1 through conduit 11 (hereinbelow, the liquid is referred to simply as "bottom liquid of column 1"), and a part of the bottom liquid of column 1 was heated by reboiler 12 to provide the energy required for distillation and returned to column bottom 10 of distillation column 1 through conduit 13, while the remainder of the bottom liquid of column 1 was withdrawn as a high boiling point mixture in a liquid form through conduit 14 at a flow rate of 234.2 g/h. The high boiling point mixture contained EG, MeOH, EC, DMC and KOH in concentrations of 69.8% by weight, 29.9% by weight, 0.19% by weight, 0.04% by weight and 0.085% by weight, respectively. The conversion of EC in the transesterification reaction in step (1) was 99.8%.

The high boiling point mixture withdrawn through conduit 14 was fed to etherification reactor 15 preheated to 170° C., which was comprised of a column having an inner diameter of 15 mm and a length of 30 cm and having packed therein Dixon packings (3 mm$\phi$), thereby effecting an etherification reaction in reactor 15, to thereby obtain an etherification reaction mixture. The obtained etherification reaction mixture contained EG, MeOH, diethylene glycol (DEG), DMC, KOH (inclusive of potassium carbonate and potassium hydrogencarbonate which are derived from KOH) and carbon dioxide in concentrations of 69.6% by weight, 29.9% by weight, 0.23% by weight, 0.04% by weight, 0.085% by weight and 0.094% by weight, respectively. No EC was detected in the etherification reaction mixture (detectable lower limit of an EC concentration in the etherification reaction mixture: 1 ppm). Therefore, the EC/EG weight ratio was less than $10^{-6}$ and the conversion of EC in step (2) was higher than 99.9%. The etherification reaction mixture was fed to low boiling point mixture separation column 17 at a position 40 cm below the top of column 17 through conduit 16 at a flow rate of 234.2 g/h, wherein column 17 was comprised of a packed column type distillation column having an inner diameter of 2.5 cm and a packing height of 120 cm and having packed therein Dixon packings (3 mm$\phi$).

Low boiling point mixture separation column 17 was operated under conditions wherein the pressure of column top 18 thereof was 1,300 Pa (10 torr) and the temperature of column bottom 26 thereof was 102° C. A low boiling point mixture in a gaseous form distilled from column top 18 of column 17 was condensed by condenser 19. A part of the resultant condensate was refluxed to column top 18 of column 17 through conduit 20 (reflux ratio: 1), while feeding the remainder of the condensate to an upper portion of carbon dioxide separation column 22 through conduit 21. From conduit 23 provided at the bottom of carbon dioxide separation column 22, nitrogen gas was introduced into the condensate, thereby bubbling the condensate with the nitrogen gas. The nitrogen gas entraining carbon dioxide was discharged from conduit 24 provided at the top of column 22. The resultant carbon dioxide-free liquid obtained in column 22 was withdrawn from conduit 25 provided at a lower portion of column 22, and recycled to continuous multi-stage distillation column 1 at the 30th stage thereof at a flow rate of 70.2 g/h. On the other hand, a liquid was withdrawn from the bottom of low boiling point mixture separation column 17 through conduit 27 (hereinbelow, the liquid is referred to simply as "bottom liquid of column 17"). The bottom liquid of column 17 contained EG, DEG and KOH (inclusive of potassium carbonate and potassium hydrogencarbonate which are derived from KOH) in concentrations of 67.6% by weight, 17.3% by weight and 15.0% by weight, respectively. 2.66 g of the bottom liquid of column 17 was withdrawn every two hours from the production system through conduit 30, while the remainder of the bottom liquid of column 17 was heated by reboiler 28 (vertical falling film evaporator) and returned to column bottom 26 of column 17 through conduit 29. Through a side-cut withdrawal port provided in the side wall of low boiling point mixture separation column 17 at a position 90 cm below the top of column 17, a distilled mixture in a gaseous form was withdrawn through conduit 31 at a flow rate of 162.2 g/h and condensed by condenser 32, to thereby obtain a side-cut condensate through conduit 33. In the obtained side-cut condensate, no compound other than EG was detected.

From the above data, it can be seen that the yield of DMC was 99.8%, the selectivity for DMC was not lower than 99%, and high purity EG was obtained in a yield of 99.6%.

COMPARATIVE EXAMPLE 1

Dimethyl carbonate (DMC) and ethylene glycol (EG) were continuously produced from ethylene carbonate (EC) and methanol (MeOH) in substantially the same manner as in Example 1, except that a high boiling point mixture withdrawn from column bottom 10 of continuous multi-stage distillation column 1 through conduit 14 was not fed to etherification reactor 15, but directely led into conduit 16 through a by path piping (not shown) connecting conduit 14 to conduit 16, thereby directly feeding the high boiling point mixture withdrawn from column 1 to low boiling point mixture separation column 17 at a position 40 cm below the top of column 17, i.e., etherification reactor 15 was not used. In the gas discharged from conduit 24 provided at the top of carbon dioxide separation column 22, no carbon dioxide was detected.

A column top condensate from column 1 was withdrawn through conduit 9 at a flow rate of 851.0 g/h, wherein the column top condensate from column 1 contained MeOH and DMC in concentrations of 67.8% by weight and 32.2% by weight, respectively. A side-cut condensate of low boiling point mixture separation column 17 was obtained through conduit 33 at a flow rate of 162.2 g/h. The obtained side-cut condensate was comprised of EG containing EC in a concentration of 0.27% by weight. A bottom liquid of column 17 was withdrawn through conduit 27. The bottom liquid of column 17 contained EG and KOH in concentrations of 81.8% by weight and 18.2% by weight, respectively. 2.2 g of the bottom liquid of column 17 was withdrawn every two hours from the production system through conduit 30, while the remainder of the bottom liquid of column 17 was heated by reboiler 28 and returned to column bottom 26 of column 17 through conduit 29.

From the above data, it can be seen that the yield of DMC was 99.8%, the selectivity for DMC was 99%, and the yield of EG was 99.8%, which are about the same results as in Example 1; however, the obtained EG contained EC and hence high purity EG was not able to be obtained.

COMPARATIVE EXAMPLE 2

Figure 2:
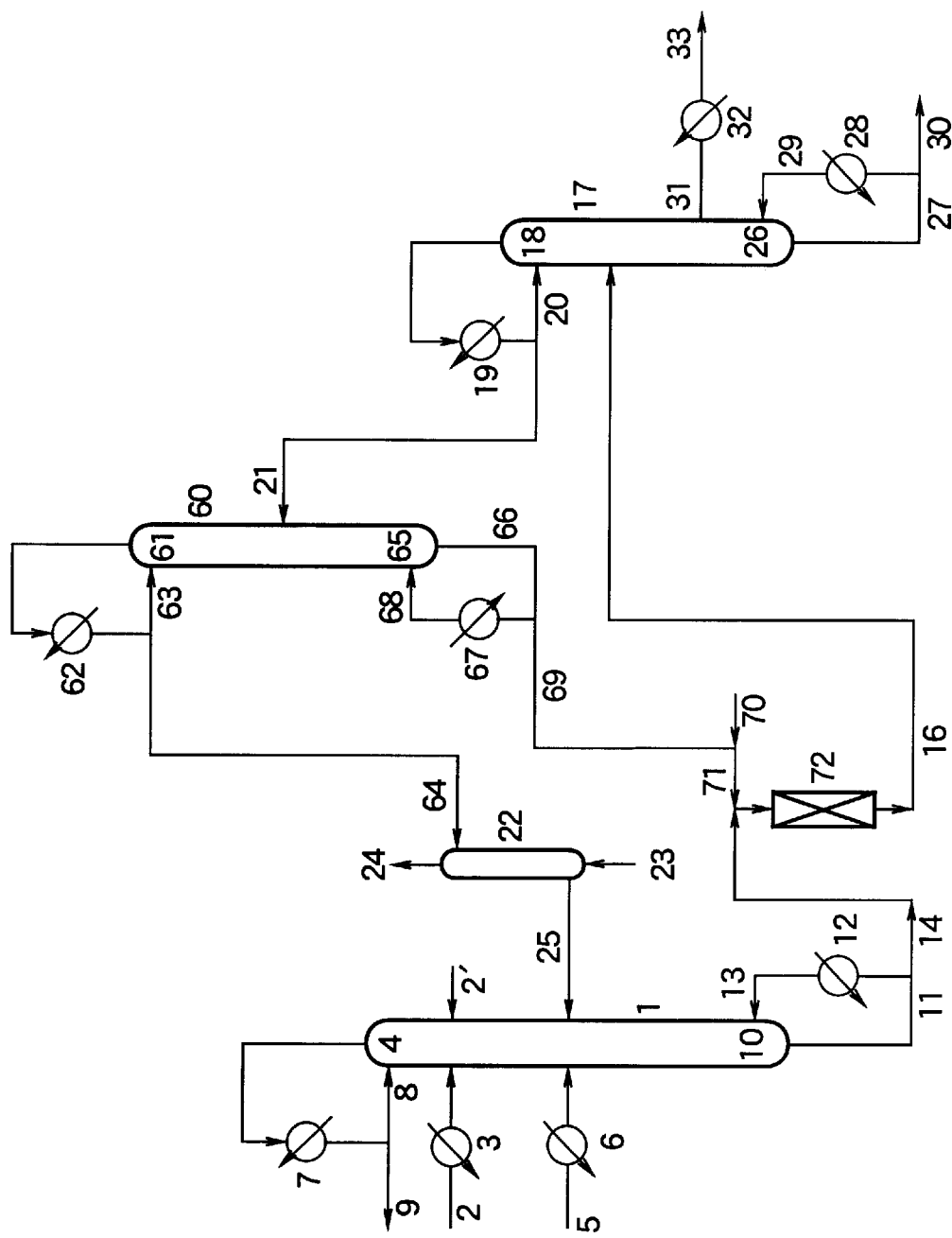
FIG. 2 is a diagram showing the system which was used for practicing Comparative Example 2 of the present application.

Using a production system as shown in FIG. 2, dimethyl carbonate (DMC) and ethylene glycol (EG) were continuously produced from ethylene carbonate (EC) and methanol (MeOH). That is, substantially the same procedure as in Example 1 was performed, except that a high boiling point mixture (containing unreacted EC remaining therein) obtained from continuous multi-stage distillation column 1 was fed to hydrolysis reactor 72 (instead of etherification reactor 15 used in Example 1), and that excess water not consumed in the hydrolysis was separated by using water separation column 60.

A column top condensate from column 1 was withdrawn through conduit 9 at a flow rate of 851.2 g/h, wherein the column top condensate from column 1 contained MeOH and DMC in concentrations of 67.7% by weight and 32.3% by weight, respectively.

A high boiling point mixture withdrawn from column bottom 10 of column 1 through conduits 11 and 14 contained EG, MeOH, EC, DMC and KOH in concentrations of 69.8% by weight, 29.9% by weight, 0.19% by weight, 0.04% by weight and 0.085% by weight, respectively. The high boiling point mixture was introduced into hydrolysis reactor 72 preheated to 180° C., together with water supplied from conduits 70 and 71 at a flow rate of 0.9 g/h, wherein reactor 72 was comprised of a column having an inner diameter of 15 mm and a length of 30 cm and having packed therein Dixon packings (3 mmφ). EC contained in the high boiling point mixture was hydrolyzed in hydrolysis reactor 72 to form EG and carbon dioxide. The resultant hydrolysis reaction mixture contained EG, MeOH, water, DMC, KOH (inclusive of potassium carbonate and potassium hydrogencarbonate which are derived from KOH) and carbon dioxide in concentrations of 69.6% by weight, 29.8% by weight, 0.34% by weight, 0.04% by weight, 0.085% by weight and 0.094% by weight, respectively. No EC was detected in the hydrolysis reaction mixture. The hydrolysis reaction mixture was fed to low boiling point mixture separation column 17 at a position 40 cm below the top of column 17 through conduit 16 at a flow rate of 235.14 g/h, wherein column 17 was the same as used in Example 1.

Low boiling point mixture separation column 17 was operated under conditions wherein the pressure of column top 18 thereof and the temperature of column bottom 26 thereof were substantially the same as in Example 1. A low boiling point mixture in a gaseous form distilled from column top 18 of column 17 was condensed by condenser 19. A part of the resultant condensate was refluxed to column top 18 of column 17 through conduit 20, while feeding the remainder of the condensate to water separation column 60 at a position 50 cm below the top of column 60 through conduit 21, wherein column 60 was comprised of a packed column type distillation column having an inner diameter of 2.5 cm and a packing height of 100 cm and having packed therein Dixon packings (3 mmφ). Water separation column 60 was operated under conditions wherein the pressure of column top 61 thereof was atmospheric pressure and the temperature of column bottom 65 thereof was 102° C. A gaseous mixture distilled from column top 61 of column 60 was condensed by condenser 62. A part of the resultant condensate was refluxed to column top 61 of column 60 through conduit 63, while feeding the remainder of the condensate to an upper portion of carbon dioxide separation column 22 through conduit 64. In carbon dioxide separation column 22, carbon dioxide was separated in substantially the same manner as in Example 1. The resultant carbon dioxide-free liquid obtained in column 22 was withdrawn from conduit 25 provided at a lower portion of column 22, and recycled to continuous multi-stage distillation column 1 at the 30th stage thereof at a flow rate of 70.2 g/h. A bottom liquid of column 17 was withdrawn through conduit 27. The bottom liquid of column 17 contained EG and KOH (inclusive of potassium carbonate and potassium hydrogencarbonate which are derived from KOH) in concentrations of 81.8% by weight and 18.2% by weight, respectively. 2.2 g of the bottom liquid of column 17 was withdrawn every two hours from the production system through conduit 30, while the remainder of the bottom liquid of column 17 was heated by reboiler 28 and returned to column bottom 26 of column 17 through conduit 29. Through a side-cut withdrawal port provided in the side wall of low boiling point mixture separation column 17 at a position 90 cm below the top of column 17, a distilled mixture in a gaseous form was withdrawn through conduit 31 at a flow rate of 162.8 g/h and condensed by condenser 32, to thereby obtain a side-cut condensate through conduit 33. In the obtained side-cut condensate, no compound other than EG was detected.

From the above data, it can be seen that the yield of DMC was 99.8%, the selectivity for DMC was not lower than 99%, and high purity EG was obtained in a yield of 99.9%. However, a comparison between Comparative Example 2 and Example 1 shows that Comparative Example 2, wherein water as an additional feedstock is needed and a water separation column is needed, requires complicated operations, differing from Example 1.

EXAMPLE 2

Dimethyl carbonate (DMC) and ethylene glycol (EG) were continuously produced from ethylene carbonate (EC) and methanol (MeOH) in substantially the same manner as in Example 1, except that the reaction conditions were as follows.

Etherification reactor 15 was preheated to 165° C. The etherification reaction mixture contained EG, MeOH, DEG, DMC, KOH (inclusive of potassium carbonate and potassium hydrogencarbonate which are derived from KOH), carbon dioxide and EC in concentrations of 69.6% by weight, 29.9% by weight, 0.225% by weight, 0.04% by weight, 0.085% by weight, 0.093% by weight and 0.0006% by weight, respectively. The etherification reaction mixture was fed to low boiling point mixture separation column 17 through conduit 16 at a flow rate of 234.24 g/h. The EC/EG weight ratio in the etherification reaction mixture was 8.6× $10^{-6}$, and the conversion of EC in step (2) was 99.6%. The reflux ratio of low boiling point mixture separation column 17 was 5. Through a side-cut withdrawal port provided in the side wall of low boiling point mixture separation column 17, a distilled mixture was withdrawn at a flow rate of 162.2 g/h which is the same value as in Example 1, and condensed to obtain a side-cut condensate. In the obtained side-cut condensate, no compound other than EG was detected.

From the above data, it can be seen that the yield of DMC was 99.8%, the selectivity for DMC was not lower than 99%, and high purity EG was obtained in a yield of 99.6%.

EXAMPLE 3

Dimethyl carbonate (DMC) and ethylene glycol (EG) were continuously produced from ethylene carbonate (EC) and methanol (MeOH) in substantially the same manner as in Example 1, except that the reaction conditions were as follows.

The reflux ratio of continuous multi-stage distillation column 1 was 0.2. A column top condensate from column 1 was withdrawn at a flow rate of 850.0 g/h, wherein the column top condensate from column 1 contained MeOH and DMC in concentrations of 68.1% by weight and 31.9% by weight, respectively. A high boiling point mixture was withdrawn from column 1 at a flow rate of 234.7 g/h, wherein the high boiling point mixture contained EG, MeOH, EC, DMC and KOH in concentrations of 68.4% by weight, 29.5% by weight, 1.97% by weight, 0.04% by weight and 0.085% by weight, respectively. The conversion of EC in step (1) was 98%.

Etherification reactor 15 was preheated to 160° C. The etherification reaction mixture contained EG, MeOH, DEG, DMC, KOH (inclusive of potassium carbonate and potassium hydrogencarbonate which are derived from KOH), carbon dioxide and EC in concentrations of 67.0% by weight, 29.5% by weight, 2.32% by weight, 0.04% by weight, 0.085% by weight, 0.96% by weight and 0.0394% by weight, respectively. The etherification reaction mixture was fed to low boiling point mixture separation column 17 through conduit 16 at a flow rate of 234.65 g/h. The EC/EG weight ratio in the etherification reaction mixture was 5.8× $10^{-4}$, and the conversion of EC in step (2) was 98%. The reflux ratio of low boiling point mixture separation column 17 was 5. Through a side-cut withdrawal port provided in the side wall of low boiling point mixture separation column 17, a distilled mixture was withdrawn at a flow rate of 156.4 g/h, and condensed to obtain a side-cut condensate. In the obtained side-cut condensate, no compound other than EG was detected.

From the above data, it can be seen that the yield of DMC was 98%, the selectivity for DMC was not lower than 99%, and high purity EG was obtained in a yield of 96.1%.

EXAMPLE 4

Dimethyl carbonate (DMC) and ethylene glycol (EG) were continuously produced from ethylene carbonate (EC) and methanol (MeOH) in substantially the same manner as in Example 1, except that the reaction conditions were as follows.

The reflux ratio of continuous multi-stage distillation column 1 was 0.2. A column top condensate from column 1 was withdrawn at a flow rate of 850.0 g/h, wherein the column top condensate from column 1 contained MeOH and DMC in concentrations of 68.1% by weight and 31.9% by weight, respectively. A high boiling point mixture was withdrawn from column 1 at a flow rate of 234.7 g/h, wherein the high boiling point mixture contained EG, MeOH, EC, DMC and KOH in concentrations of 68.4% by weight, 29.5% by weight, 1.97% by weight, 0.04% by weight and 0.085% by weight, respectively. The conversion of EC in step (1) was 98%.

Etherification reactor 15 was preheated to 155° C. The etherification reaction mixture contained EG, MeOH, DEG, DMC, KOH (inclusive of potassium carbonate and potassium hydrogencarbonate which are derived from KOH), carbon dioxide and EC in concentrations of 67.1% by weight, 29.5% by weight, 2.28% by weight, 0.04% by weight, 0.085% by weight, 0.95% by weight and 0.079% by weight, respectively. The etherification reaction mixture was fed to low boiling point mixture separation column 17 through conduit 16 at a flow rate of 234.66 g/h. The EC/EG weight ratio in the etherification reaction mixture was $1.1 \times 10^{-3}$, and the conversion of EC in step (2) was 96%. The reflux ratio of low boiling point mixture separation column 17 was 5. Through a side-cut withdrawal port provided in the side wall of low boiling point mixture separation column 17, a distilled mixture was withdrawn at a flow rate of 156.4 g/h, and condensed to obtain a side-cut condensate. In the obtained side-cut condensate, no compound other than EG was detected.

From the above data, it can be seen that the yield of DMC was 98%, the selectivity for DMC was not lower than 99%, and high purity EG was obtained in a yield of 96.1%.

COMPARATIVE EXAMPLE 3

Dimethyl carbonate (DMC) and ethylene glycol (EG) were continuously produced from ethylene carbonate (EC) and methanol (MeOH) in substantially the same manner as in Example 4, except that the reaction conditions were as follows.

Etherification reactor 15 was preheated to 78° C. The etherification reaction mixture contained EG, MeOH, DEG, DMC, KOH (inclusive of potassium carbonate and potassium hydrogencarbonate which are derived from KOH), carbon dioxide and EC in concentrations of 68.1% by weight, 29.5% by weight, 0.47% by weight, 0.04% by weight, 0.085% by weight, 0.20% by weight and 1.58% by weight, respectively. The etherification reaction mixture was fed to low boiling point mixture separation column 17 through conduit 16 at a flow rate of 234.66 g/h. The EC/EG weight ratio in the etherification reaction mixture was $2.3 \times 10^{-2}$, and the conversion of EC in step (2) was 20%.

Through a side-cut withdrawal port provided in the side wall of low boiling point mixture separation column 17, a distilled mixture was withdrawn through conduit 31 at a flow rate of 158.9 g/h, and condensed to obtain a side-cut condensate. The obtained side-cut condensate was comprised of EG containing EC in a concentration of 0.0043% by weight.

From the above data, it can be seen that the yield of DMC was 98%, the selectivity for DMC was not lower than 99%, and the yield of EG was 97.6%, which are about the same results as in Example 1; however, the obtained EG contained EC and hence high purity EG was not be able to be obtained.

EXAMPLE 5

Figure 3:
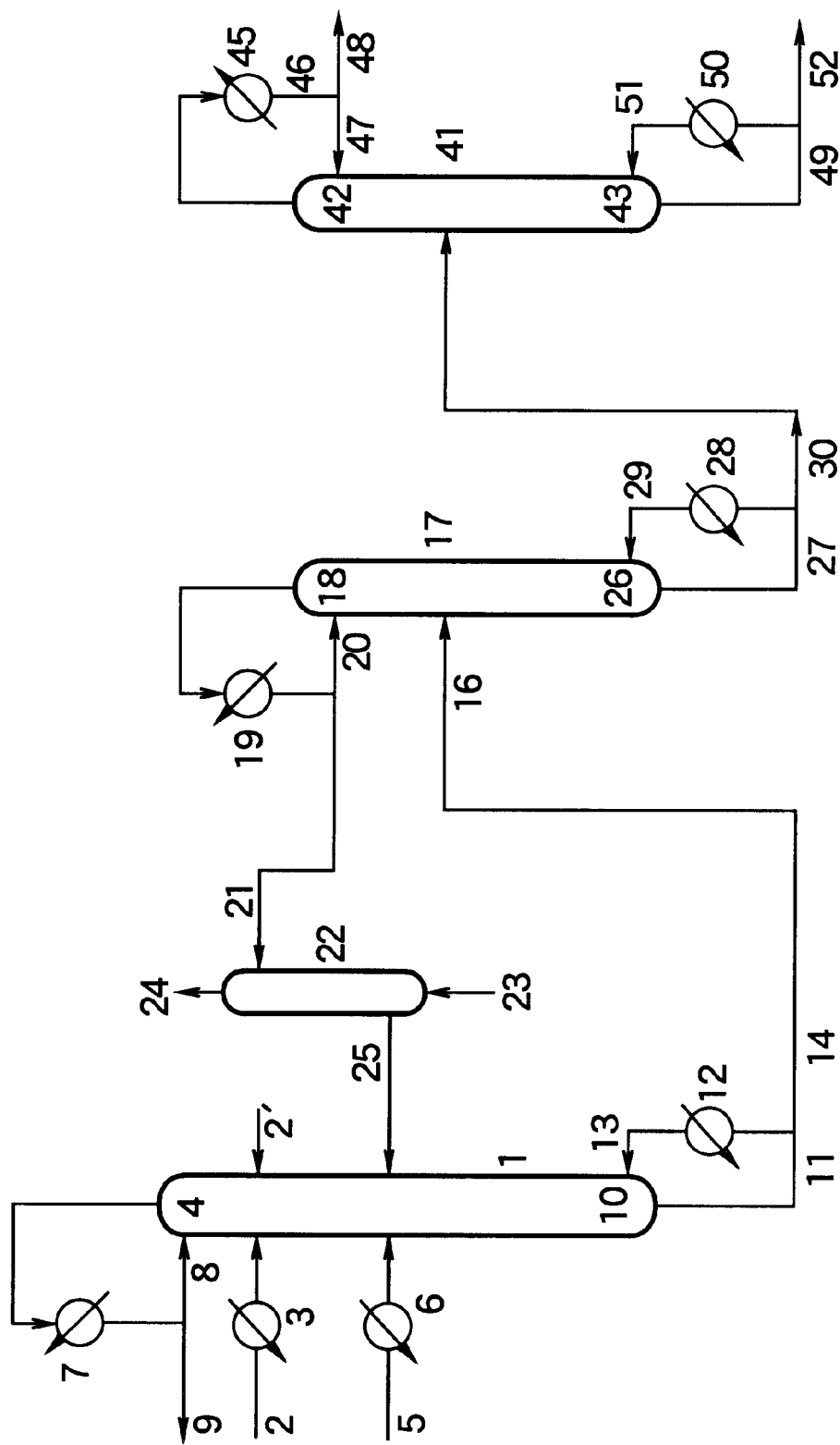
FIG. 3 is a diagram showing the system which was used for practicing Example 5 of the present application.

Using a production system as shown in FIG. 3, dimethyl carbonate (DMC) and ethylene glycol (EG) were continuously produced from ethylene carbonate (EC) and methanol (MeOH).

The same continuous multi-stage distillation column 1 as used in Example 1 and the same low boiling point mixture separation column (low boiling point mixture separation/etherification column) 17 as used in Example 1, were used. Continuous multi-stage distillation column 1 was operated in substantially the same manner as in Example 1, except that the mixture of MeOH and DMC, which was fed in a liquid form through conduit 5 and preheater 6, had an MeOH/DMC weight ratio of 97/3, and the flow rate of the mixture of MeOH and DMC was 735.0 g/h.

A column top condensate from column 1 was withdrawn through conduit 9 at a flow rate of 803.1 g/h, wherein the column top condensate from column 1 contained MeOH and DMC in concentrations of 67.9% by weight and 32.1% by weight, respectively. The reflux ratio of column 1 was 0.4. On the other hand, a bottom liquid of column 1 was withdrawn from column bottom 10 through conduit 11, and a part of the bottom liquid of column 1 was heated by reboiler 12 and returned to column bottom 10 of column 1 through conduit 13, while the remainder of the bottom liquid of column 1 was withdrawn as a high boiling point mixture through conduit 14 at a flow rate of 231.3 g/h and fed to low boiling point mixture separation column 17 at a position 40 cm below the top of column 17. The high boiling point mixture contained EG, MeOH, EC, DMC and KOH in concentrations of 70.7% by weight, 29.1% by weight, 0.099% by weight, 0.04% by weight and 0.086% by weight, respectively. The conversion of EC in the transesterification reaction in step (1) was 99.9%.

Low boiling point mixture separation column 17 was operated in substantially the same manner as in Example 1, except:

that the pressure of column top 18 of column 17 was atmospheric pressure, and the pressure and temperature of column bottom 26 of column 17 were 102,600 Pa (770 torr) and 201° C., respectively, thereby causing column bottom 26 thereof to serve as an etherification reactor, and that the withdrawal of the produced EG from column 17 was conducted through conduit 27 provided at column bottom 26, but not through the side-cut withdrawal port of column 17.

A low boiling point mixture distilled from column top 18 of low boiling point mixture separation column 17 was condensed by condenser 19. A part of the resultant condensate was refluxed to column top 18 of column 17 through conduit 20, while feeding the remainder of the condensate to an upper portion of carbon dioxide separation column 22 through conduit 21, wherein column 22 was the same as used in Example 1. The resultant carbon dioxide-free liquid obtained in column 22 was withdrawn from conduit 25 and recycled to continuous multi-stage distillation column 1 at the 30th stage thereof at a flow rate of 70.2 g/h. The residence time at column bottom 26 of low boiling point mixture separation column 17 was 1.5 hours. A bottom liquid of column 17 was withdrawn through conduit 27. A part of the bottom liquid of column 17 was heated by reboiler 28 (double-pipe heat exchanger) and returned to column bottom 26 of column 17 through conduit 29, while the remainder of the bottom liquid of column 17 was withdrawn as an etherification reaction mixture through conduit 30 at a flow rate of 163.9 g/h. The obtained etherification reaction mixture contained EG, DEG and KOH (inclusive of potassium carbonate and potassium hydrogencarbonate which are derived from KOH) in concentrations of 99.7% by weight, 0.17% by weight and 0.12% by weight, respectively. No EC was detected in the etherification reaction mixture. Therefore, the EC/EG weight ratio was less than $10^{-6}$ and the conversion of EC in step (2) was higher than 99.9%.

The etherification reaction mixture was fed to EG purification column 41 at a position 90 cm below the top of column 41 through conduit 30, wherein column 41 was comprised of a packed column type distillation column having an inner diameter of 2.5 cm and a packing height of 120 cm and having packed therein Dixon packings (3 mmφ).

EG purification column 41 was operated under conditions wherein the pressure of column top 42 thereof was 4,000 Pa (30 torr) and the temperature of column bottom 43 thereof was 122.5° C. A gaseous mixture distilled from column top 42 of column 41 was condensed by condenser 45. A part of the resultant condensate was refluxed to column top 42 of column 41 through conduit 47 (reflux ratio: 0.5), while withdrawing the remainder of the condensate through conduit 48 as a column top condensate at a flow rate of 162.5 g/h. In the column top condensate obtained from column 41, no compound other than EG was detected.

A liquid was withdrawn from the bottom of EG purification column 41 through conduit 49 (hereinbelow, the liquid is referred to simply as "bottom liquid of column 41"). The bottom liquid of column 41 contained EG, DEG and KOH (inclusive of potassium carbonate and potassium hydrogencarbonate which are derived from KOH) in concentrations of 65.2% by weight, 20.3% by weight and 14.5% by weight, respectively. 2.8 g of the bottom liquid of column 41 was withdrawn every two hours from the production system through conduit 52, while the remainder of the bottom liquid of column 41 was heated by reboiler 50 and returned to column bottom 43 of column 41 through conduit 51.

From the above data, it can be seen that the yield of DMC was 99.9%, the selectivity for DMC was not lower than 99%, and high purity EG was obtained in a yield of 99.8%.

COMPARATIVE EXAMPLE 4

Dimethyl carbonate (DMC) and ethylene glycol (EG) were continuously produced from ethylene carbonate (EC) and methanol (MeOH) in substantially the same manner as in Example 5, except:

that the pressure of column top 18 of low boiling point mixture separation column 17 was 1,300 Pa (10 torr), and the pressure and temperature of column bottom 26 of column 17 were 2,660 Pa (20 torr) and 99° C., respectively, and that, as reboiler 28, a vertical falling film evaporator was used, thereby causing the residence time at column bottom 26 of column 17 to be 0.15 hour. That is, differing from the case of Example 5, in this Comparative Example 4, column bottom 26 of low boiling point mixture separation column 17 was not caused to serve as an etherification reactor.

A bottom liquid of column 1 was withdrawn from column bottom 10 through conduit 11, and a part of the bottom liquid of column 1 was heated by reboiler 12 and returned to column bottom 10 of column 1 through conduit 13, while the remainder of the bottom liquid of column 1 was withdrawn as a high boiling point mixture through conduit 14 at a flow rate of 231.2 g/h. The high boiling point mixture contained EG, MeOH, EC, DMC and KOH in concentrations of 70.6% by weight, 29.1% by weight, 0.099% by weight, 0.04% by weight and 0.086% by weight, respectively. The conversion of EC in the transesterification reaction in step (1) was 99.9%.

A column top condensate from column 1 was withdrawn through conduit 9 at a flow rate of 803.1 g/h, wherein the column top condensate from column 1 contained MeOH and DMC in concentrations of 67.9% by weight and 32.1% by weight, respectively. In the gas discharged from conduit 24 provided at the top of carbon dioxide separation column 22, no carbon dioxide was detected. A part of the bottom liquid of column 17 was heated by reboiler 28 and returned to column bottom 26 of column 17 through conduit 29, while the remainder of the bottom liquid of column 17 was withdrawn through conduit 30 at a flow rate of 163.9 g/h.

The bottom liquid of column 17 contained EG, EC and KOH in concentrations of 99.7% by weight, 0.14% by weight and 0.12% by weight, respectively. A column top condensate of EG purification column 41 was withdrawn through conduit 48 at a flow rate of 162.7 g/h. The column top condensate obtained from column 41 was comprised of EG containing EC in a concentration of 34 ppm by weight. A bottom liquid of column 41 was withdrawn from the bottom of column 41 through conduit 49. The bottom liquid of column 41 contained EG, EC and KOH in concentrations of 67.7% by weight, 17.3% by weight and 15.0% by weight, respectively. 2.7 g of the bottom liquid of column 41 was withdrawn every two hours from the production system through conduit 52, while the remainder of the bottom liquid of column 41 was heated by reboiler 50 and returned to column bottom 43 of column 41 through conduit 51.

From the above data, it can be seen that the yield of DMC was 99.9%, the selectivity for DMC was not lower than 99%, and the yield of EG was 99.9%, which are about the same results as in Example 1; however, the obtained EG contained EC and hence high purity EG was not able to be obtained.

EXAMPLE 6

Figure 4:
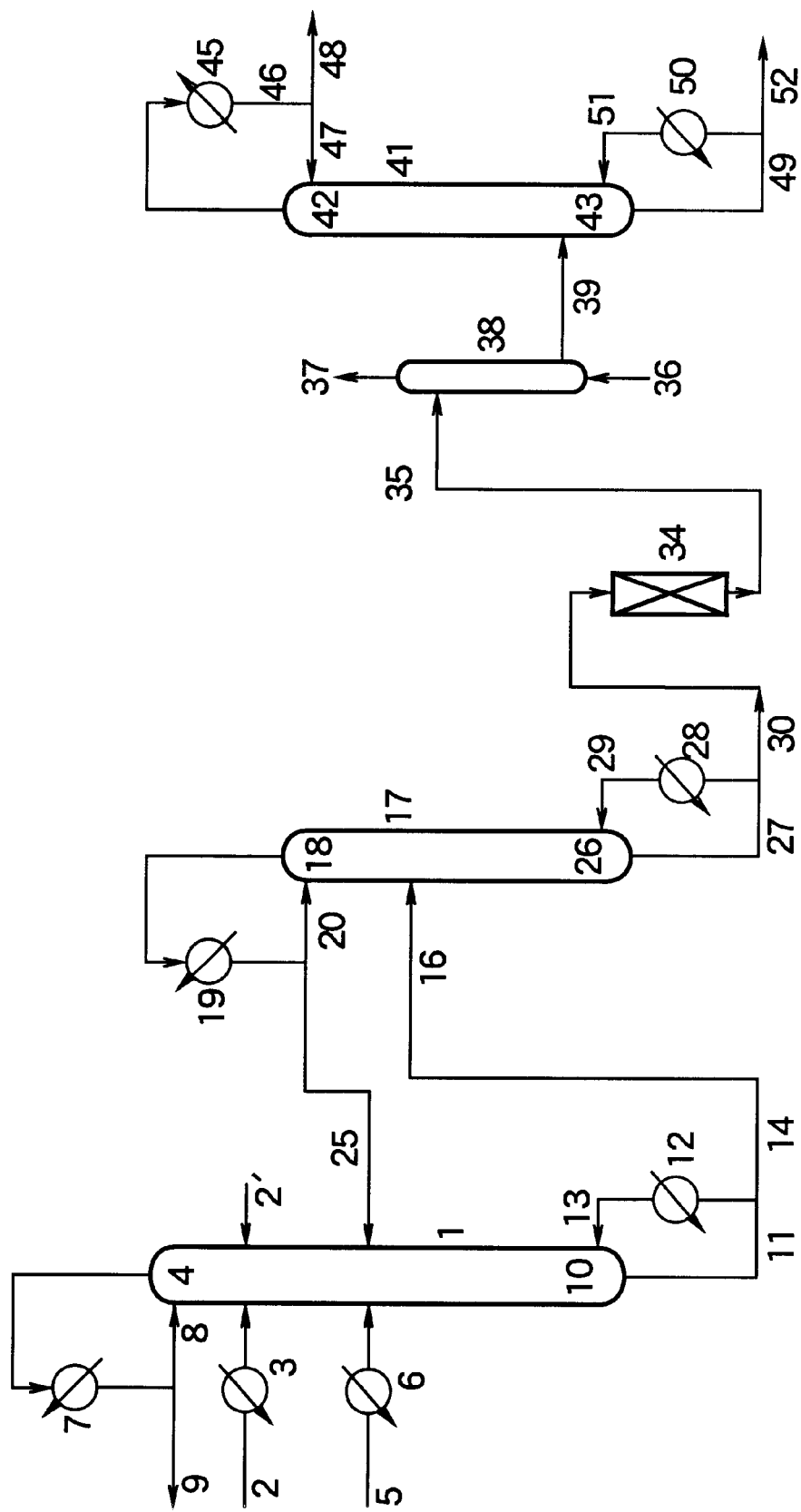
FIG. 4 is a diagram showing the system which was used for practicing Example 6 of the present application.

Using a production system as shown in FIG. 4, dimethyl carbonate (DMC) and ethylene glycol (EG) were continuously produced from ethylene carbonate (EC) and methanol (MeOH).

The same continuous multi-stage distillation column 1 as used in Example 5 and the same low boiling point mixture separation column 17 as used in Example 5, were used. Continuous multi-stage distillation column 1 was operated in substantially the same manner as in Example 5.

A low boiling point mixture in a gaseous form distilled from column top 4 of distillation column 1 was condensed by condenser 7. A part of the resultant condensate was refluxed to column top 4 of distillation column 1 through conduit 8, while withdrawing the remainder of the condensate through conduit 9 as a column top condensate from column 1 at a flow rate of 803.3 g/h, wherein the column top condensate from column 1 contained MeOH and DMC in concentrations of 67.9% by weight and 32.1% by weight, respectively. On the other hand, a bottom liquid of column 1 was withdrawn from column bottom 10 of column 1 through conduit 11, and a part of the bottom liquid of column 1 was returned to column bottom 10 of column 1 through reboiler 12 and conduit 13, while the remainder of the bottom liquid of column 1 was withdrawn as a high boiling point mixture through conduit 14 at a flow rate of 231.3 g/h and fed to low boiling point mixture separation column 17 at a position 40 cm below the top of column 17 through conduit 16. The high boiling point mixture contained EG, MeOH, EC, DMC and KOH in concentrations of 70.7% by weight, 29.1% by weight, 0.099% by weight, 0.04% by weight and 0.086% by weight, respectively. The conversion of EC in step (1) was 99.9%.

Low boiling point mixture separation column 17 was operated in substantially the same manner as in Example 5, except:

that the pressure of column top 18 of column 17 was 1,300 Pa (10 torr), and the pressure and temperature of column bottom 26 of column 17 were 2,660 Pa (20 torr) and 99° C., respectively, and that, as reboiler 28, a vertical falling film evaporator was used, thereby causing the residence time at column bottom 26 of column 17 to be 0.15 hour. That is, differing from the case of Example 5, in this Example 6, column bottom 26 of low boiling point mixture separation column 17 was not caused to serve as an etherification reactor. A low boiling point mixture distilled from column top 18 of column 17 was condensed by condenser 19. A part of the resultant condensate was refluxed to column top 18 of column 17 through conduit 20, while recycling the remainder of the condensate to continuous multi-stage distillation column 1 at the 30th stage thereof through conduit 25 at a flow rate of 67.3 g/h. A part of the bottom liquid of column 17 was heated by reboiler 28 and returned to column bottom 26 of column 17 through conduit 29, while the remainder of the bottom liquid of column 17 was withdrawn through conduit 30 at a flow rate of 164.0 g/h. The bottom liquid of column 17 contained EG, EC and KOH in concentrations of 99.7% by weight, 0.14% by weight and 0.12% by weight, respectively. The bottom liquid of column 17 withdrawn through conduit 30 was fed to etherification reactor 34 (which is the same as etherification reactor 15 used in Example 1) preheated to 180° C., thereby effecting an etherification reaction in reactor 34, to thereby obtain an etherification reaction mixture. The obtained etherification reaction mixture contained EG, DEG, KOH (inclusive of potassium carbonate and potassium hydrogencarbonate which are derived from KOH) and carbon dioxide in concentrations of 99.7% by weight, 0.17% by weight, 0.12% by weight and 0.073% by weight, respectively. No EC was detected in the etherification reaction mixture. Therefore, the EC/EG weight ratio was less than $10^{-6}$ and the conversion of EC in step (2) was higher than 99.9%. The etherification reaction mixture was fed to an upper portion of carbon dioxide separation column 38 through conduit 35. From conduit 36 provided at the bottom of carbon dioxide separation column 38, nitrogen gas was introduced into the etherification reaction mixture, thereby bubbling the mixture with the nitrogen gas. The nitrogen gas entraining carbon dioxide was discharged from conduit 37 provided at the top of column 38. The resultant carbon dioxide-free liquid obtained in column 38 was withdrawn from conduit 39 provided at a lower portion of column 38, and fed to EG purification column 41 at a position 90 cm below the top of column 41, wherein column 41 was the same as used in Example 5.

EG purification column 41 was operated in substantially the same manner as in Example 5. A column top condensate of EG purification column 41 was withdrawn through conduit 48 at a flow rate of 162.4 g/h. In the column top condensate obtained from column 41, no compound other than EG was detected. A bottom liquid of column 41 was withdrawn from the bottom of column 41

22, 38 carbon dioxide separation column 41 diol (ethylene glycol) purification column through conduit 49, wherein the bottom liquid of column 41 contained EG, DEG and KOH (inclusive of potassium carbonate and potassium hydrogencarbonate which are derived from KOH) in concentrations of 65.2% by weight, 20.4% by weight and 14.4% by weight, respectively. 2.8 g of the bottom liquid of column 41 was withdrawn every two hours from the production system through conduit 52, while the remainder of the bottom liquid of column 41 was heated by reboiler 50 and returned to column bottom 43 of column 41 through conduit 51.

From the above data, it can be seen that the yield of DMC was 99.9%, the selectivity for DMC was not lower than 99%, and high purity EG was obtained in a yield of 99.8%.

EXAMPLE 7

Dimethyl carbonate (DMC) and ethylene glycol (EG) were continuously produced from ethylene carbonate (EC) and methanol (MeOH) in substantially the same manner as in Example 5, except that an 18 wt. % solution of sodium hydroxide (as a catalyst) in ethylene glycol was used instead of an 18 wt. % solution of potassium hydroxide (as a catalyst) in ethylene glycol.

A column top condensate from continuous multi-stage distillation column 1 was withdrawn through conduit 9 at a flow rate of 803.1 g/h, wherein the column top condensate from column 1 contained MeOH and DMC in concentrations of 67.9% by weight and 32.1% by weight, respectively (these date are the same as in Example 5).

A high boiling point mixture was withdrawn from column 1 at a flow rate of 231.3 g/h, wherein the high boiling point mixture contained EG, MeOH, EC, DMC and NaOH in concentrations of 70.7% by weight, 29.1% by weight, 0.099% by weight, 0.04% by weight and 0.086% by weight, respectively. The conversion of EC in step (1) was 99.9%.

An etherification reaction mixture was obtained through conduit 30 as a bottom liquid of low boiling point mixture separation column (low boiling point mixture separation/etherification column) 17. The etherification reaction mixture contained EG, DEG and NaOH (inclusive of sodium carbonate and sodium hydrogencarbonate which are derived from NaOH) in concentrations of 99.7% by weight, 0.17% by weight and 0.12% by weight, respectively. The etherification reaction mixture was fed to EG purification column 41 through conduit 30 at a flow rate of 163.9 g/h. No EC was detected in the etherification reaction mixture. Therefore, the EC/EG weight ratio was less than $10^{-6}$ and the conversion of EC in step (2) was higher than 99.9%.

A column top condensate of EG purification column 41 was withdrawn through conduit 48 at a flow rate of 162.3 g/h. In the column top condensate obtained from column 41, no compound other than EG was detected. A bottom liquid of column 41 was withdrawn from the bottom of column 41 through conduit 49, wherein the bottom liquid of column 41 contained EG, DEG and NaOH in concentrations of 65.3% by weight, 20.2% by weight and 14.5% by weight, respectively. 2.8 g of the bottom liquid of column 41 was withdrawn every two hours from the production system through conduit 52, while the remainder of the bottom liquid of column 41 was heated by reboiler 50 and returned to column bottom 43 of column 41 through conduit 51.

From the above data, it can be seen that the yield of DMC was 99.9%, the selectivity for DMC was not lower than 99%, and high purity EG was obtained in a yield of 99.8%.

EXAMPLE 8

Dimethyl carbonate (DMC) and ethylene glycol (EG) were continuously produced from ethylene carbonate (EC) and methanol (MeOH) in substantially the same manner as in Example 5, except that the mixture of MeOH and DMC, which was fed to column 1 in a liquid form through conduit 5 and preheater 6, had an MeOH/DMC weight ratio of 90/10, and the flow rate of the mixture of MeOH and DMC was 966.2 g/h.

A column top condensate from continuous multi-stage distillation column 1 was withdrawn through conduit 9 at a flow rate of 1034.1 g/h, wherein the column top condensate from column 1 contained MeOH and DMC in concentrations of 67.9% by weight and 32.1% by weight, respectively. A high boiling point mixture was withdrawn from column bottom 10 of column 1 through conduit 14 at a flow rate of 229.5 g/h, wherein the high boiling point mixture contained EG, MeOH, EC, DMC and KOH in concentrations of 71.1% by weight, 28.4% by weight, 0.40% by weight, 0.04% by weight and 0.087% by weight, respectively. The conversion of EC in step (1) was 99.6%.

A low boiling point mixture distilled from column top 18 of low boiling point mixture separation column (low boiling point mixture separation/etherification column) 17 was condensed by condenser 19. A part of the resultant condensate was refluxed to column top 18 of column 17 through conduit 20, while feeding the remainder of the condensate to an upper portion of carbon dioxide separation column 22 through conduit 21. The resultant carbon dioxide-free liquid obtained in column 22 was withdrawn from conduit 25 and recycled to continuous multi-stage distillation column 1 at the 30th stage thereof at a flow rate of 65.3 g/h.

An etherification reaction mixture was obtained through conduit 30 as a bottom liquid of low boiling point mixture separation column (low boiling point mixture separation/etherification column) 17. The etherification reaction mixture contained EG, DEG and KOH (inclusive of potassium carbonate and potassium hydrogencarbonate which are derived from KOH) in concentrations of 99.2% by weight, 0.68% by weight and 0.12% by weight, respectively. The etherification reaction mixture was fed to EG purification column 41 through conduit 30 at a flow rate of 163.8 g/h. No EC was detected in the etherification reaction mixture. Therefore, the EC/EG weight ratio was less than $10^{-6}$ and the conversion of EC in step (2) was higher than 99.9%.

A column top condensate of EG purification column 41 was withdrawn through conduit 48 at a flow rate of 161.5 g/h. In the column top condensate obtained from column 41, no compound other than EG was detected. A bottom liquid of column 41 was withdrawn from the bottom of column 41 through conduit 49, wherein the bottom liquid of column 41 contained EG, DEG and KOH (inclusive of potassium carbonate and potassium hydrogencarbonate which are derived from KOH) in concentrations of 40.7% by weight, 50.2% by weight and 9.1% by weight, respectively. 4.4 g of the bottom liquid of column 41 was withdrawn every two hours from the production system through conduit 52, while the remainder of the bottom liquid of column 41 was heated by reboiler 50 and returned to column bottom 43 of column 41 through conduit 51.

From the above data, it can be seen that the yield of DMC was 99.6%, the selectivity for DMC was 99.6%, and high purity EG was obtained in a yield of 99.2%.

EXAMPLE 9

Figure 5:
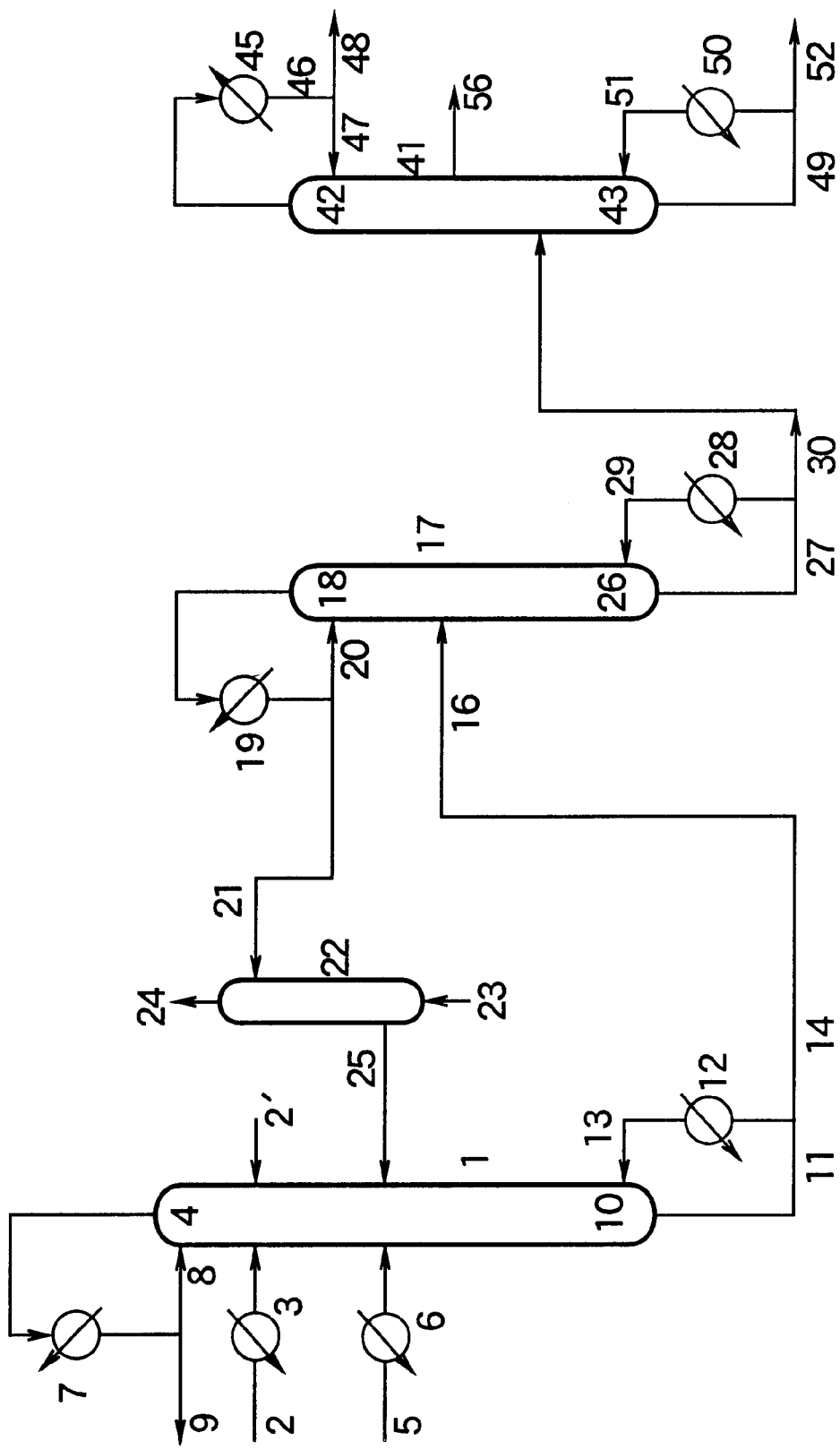
FIG. 5 is a diagram showing the system which was used for practicing Example 9 of the present application.

Dimethyl carbonate (DMC) and ethylene glycol (EG) were continuously produced from ethylene carbonate (EC) and methanol (MeOH) in substantially the same manner as in Example 8, except that a production system as shown in FIG. 5 was used and the reaction conditions were as follows.

The number of the stages of continuous multi-stage distillation column 1 was 20. A mixture of MeOH and DMC (MeOH/DMC weight ratio=90/10) was continuously fed in a liquid form to distillation column 1 at the 10th stage thereof through conduit 5 and preheater 6.

A low boiling point mixture in a gaseous form distilled from column top 4 of distillation column 1 was condensed by condenser 7. A part of the resultant condensate was refluxed to column top 4 of distillation column 1 through conduit 8, while withdrawing the remainder of the condensate through conduit 9 as a column top condensate from column 1 at a flow rate of 1031.0 g/h, wherein the column top condensate from column 1 contained MeOH and DMC in concentrations of 68.9% by weight and 31.1% by weight, respectively. On the other hand, a bottom liquid of column 1 was withdrawn from column bottom 10 through conduit 11, and a part of the bottom liquid of column 1 was heated by reboiler 12 and returned to column bottom 10 of column 1 through conduit 13, while the remainder of the bottom liquid of column 1 was withdrawn as a high boiling point mixture through conduit 14 at a flow rate of 234.3 g/h. The high boiling point mixture contained EG, MeOH, EC, DMC and KOH in concentrations of 66.3% by weight, 28.6% by weight, 4.93% by weight, 0.04% by weight and 0.085% by weight, respectively. The conversion of EC in step (1) was 95%.

Low boiling point mixture separation column (low boiling point mixture separation/etherification column) 17 was operated under conditions wherein the pressure of column top 18 of column 17 was atmospheric pressure, and the pressure and temperature of column bottom 26 of column 17 were respectively 102,600 Pa (770 torr) and 201° C., and the residence time at column bottom 26 of column 17 was 0.5 hour. A bottom liquid of column 17 was withdrawn through conduit 27. A part of the bottom liquid of column 17 was heated by reboiler 28 and returned to column bottom 26 of column 17 through conduit 29, while the remainder of the bottom liquid of column 17 was withdrawn as an etherification reaction mixture through conduit 30 at a flow rate of 161.95 g/h. The obtained etherification reaction mixture contained EG, DEG, KOH (inclusive of potassium carbonate and potassium hydrogencarbonate which are derived from KOH) and EC in concentrations of 91.4% by weight, 7.73% by weight, 0.12% by weight and 0.72% by weight, respectively. The EC/EG weight ratio in the etherification reaction mixture was $7.9 \times 10^{-3}$, and the conversion of EC in step (2) was 90%.

The packing height of EG purification column 41 was 200 cm. The etherification reaction mixture was fed to EG purification column 41 at a position 170 cm below the top of column 41 through conduit 30. EG purification column 41 was operated under conditions wherein the pressure of column top 42 thereof was 1,330 Pa (10 torr) and the temperature of column bottom 43 thereof was 135.3° C. Through a side-cut withdrawal port provided in the side wall of EG purification column 41 at a position 90 cm below the top of column 41, a liquid was withdrawn through conduit 56 at a flow rate of 140.0 g/h to thereby obtain a side-cut liquid. In the obtained side-cut liquid, no compound other than EG was detected. A gaseous mixture distilled from column top 42 of column 41 was condensed by condenser 45. A part of the resultant condensate was refluxed to column top 42 of column 41 through conduit 47 (reflux ratio: 5), while withdrawing the remainder of the condensate through conduit 48 as a column top condensate at a flow rate of 8.4 g/h. The column top condensate obtained from column 41 contained EG and EC in concentrations of 86.1% by weight and 13.9% by weight, respectively. A bottom liquid of EG purification column 41 was withdrawn from bottom 43 of column 41 through conduit 49. The bottom liquid of column 41 contained EG, DEG and KOH (inclusive of potassium carbonate and potassium hydrogencarbonate which are derived from KOH) in concentrations of 6.6% by weight, 91.9% by weight and 1.5% by weight, respectively. A part of the bottom liquid of column 41 was heated by reboiler 50 and returned to column bottom 43 of column 41 through conduit 51, while the remainder of the bottom liquid of column 41 was withdrawn from the production system through conduit 52 at a flow rate of 13.6 g/h.

From the above data, it can be seen that the yield of DMC was 95%, the selectivity for DMC was not lower than 99%, and high purity EG was obtained in a yield of 86%. The mixture of EG and EC obtained as a column top condensate from EG purification column 41 can be used as a feedstock for the transesterification reaction.

COMPARATIVE EXAMPLE 5

Dimethyl carbonate (DMC) and ethylene glycol (EG) were continuously produced from ethylene carbonate (EC) and methanol (MeOH) in substantially the same manner as in Example 9, except that the reaction conditions were as follows.

A column top condensate from continuous multi-stage distillation column 1 was withdrawn through conduit 9 at a flow rate of 1030.8 g/h, wherein the column top condensate from column 1 contained MeOH and DMC in concentrations of 68.9% by weight and 31.1% by weight, respectively. A high boiling point mixture was withdrawn from column 1 through conduit 14 at a flow rate of 234.2 g/h, wherein the high boiling point mixture contained EG, MeOH, EC, DMC and KOH in concentrations of 66.3% by weight, 28.6% by weight, 4.92% by weight, 0.04% by weight and 0.085% by weight, respectively. The conversion of EC in step (1) was 95%.

Low boiling point mixture separation column (low boiling point mixture separation/etherification column) 17 was operated under conditions wherein the pressure of column top 18 of column 17 was 3,870 Pa (29 torr), and the pressure and temperature of column bottom 26 of column 17 were 5,190 Pa (39 torr) and 120° C., respectively. An etherification reaction mixture was obtained through conduit 30 as a bottom liquid of low boiling point mixture separation column (low boiling point mixture separation/etherification column) 17. The etherification reaction mixture contained EG, DEG, EC and KOH (inclusive of potassium carbonate and potassium hydrogencarbonate which are derived from KOH) in concentrations of 92.6% by weight, 1.67% by weight, 5.57% by weight and 0.12% by weight, respectively. The etherification reaction mixture was fed to EG purification column 41 through conduit 30 at a flow rate of 166.0 g/h. The EC/EG weight ratio in the etherification reaction mixture was $6 \times 10^{-2}$, and the conversion of EC in step (2) was 20%.

The temperature of column bottom 43 of EG purification column 41 was 108.7° C. Through a side-cut withdrawal port provided in the side wall of EG purification column 41 at a position 90 cm below the top of column 41, a liquid was withdrawn through conduit 56 at a flow rate of 85.9 g/h to thereby obtain a side-cut liquid. The obtained side-cut liquid contained EC in a concentration of 0.0042% by weight. A gaseous mixture distilled from column top 42 of column 41 was condensed by condenser 45. A part of the resultant condensate was refluxed to column top 42 of column 41 through conduit 47, while withdrawing the remainder of the condensate through conduit 48 as a column top condensate at a flow rate of 66.4 g/h. The column top condensate obtained from column 41 contained EG and EC in concentrations of 86.2% by weight and 13.8% by weight, respectively. A bottom liquid of EG purification column 41 was withdrawn from bottom 43 of column 41 through conduit 49. The bottom liquid of column 41 contained EG, DEG and KOH (inclusive of potassium carbonate and potassium hydrogencarbonate which are derived from KOH) in concentrations of 78.1% by weight, 20.4% by weight and 1.5% by weight, respectively. A part of the bottom liquid of column 41 was heated by reboiler 50 and returned to column bottom 43 of column 41 through conduit 51, while the remainder of the bottom liquid of column 41 was withdrawn from the production system through conduit 52 at a flow rate of 13.6 g/h.

From the above data, it can be seen that the yield of DMC was 95% and the selectivity for DMC was not less than 99%, which are about the same results as in Example 9; however, the yield of EG was as low as 53%, and the obtained EG contained EC and hence high purity EG was not able to be obtained.

It can also be seen that the EG/EC weight ratio in a column top condensate obtained from EG purification column 41 through conduit 48 is about the same as in Example 9; however, the flow rate (at conduit 48) of the column top condensate from EG purification column 41 in Comparative Example 5 is 7.9 times as large as that in Example 9 (66.4/8.4=7.9). Accordingly, in this Comparative Example 5, when it is intended to recycle an EG/EC mixture obtained as a column top condensate from EG purification column 41 to the transesterification reaction system as a feedstock, a large amount of EG needs to be returned to the transesterification reaction system, as compared to that in the case of Example 9.

INDUSTRIAL APPLICABILITY

By the method of the present invention, in a continuous process for producing a dialkyl carbonate and a diol from a cyclic carbonate and an aliphatic monohydric alcohol, a high purity diol can be easily obtained without a need for a complicated distillation-separation step or a need for additional materials other than feedstocks and a catalyst in the transesterification.

What is claimed is:

1. A method for continuously producing a dialkyl carbonate and a diol from a cyclic carbonate and an aliphatic monohydric alcohol, comprising:

(1) continuously feeding a cyclic carbonate represented by the following formula (A):

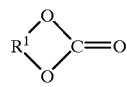

(A)

wherein $R^1$ is a divalent group which is represented by the formula —$(CH_2)_m$—, wherein m is an integer of from 2 to 6, and which is unsubstituted or substituted with at least one substituent selected from the group consisting of a $C_1$–$C_{10}$ alkyl group and a $C_6$–$C_{10}$ aryl group, and an aliphatic monohydric alcohol represented by the following formula (B):

$R^2OH$ (B)

wherein $R^2$ is a monovalent aliphatic $C_1$–$C_{12}$ hydrocarbon group which is unsubstituted or substituted with at least one substituent selected from the group consisting of a $C_1$–$C_{10}$ alkyl group and a $C_6$–$C_{10}$ aryl group, to a continuous multi-stage distillation column, and continuously effecting a transesterification between said cyclic carbonate and said aliphatic monohydric alcohol in the presence of a transesterification catalyst in said multi-stage distillation column, thereby continuously producing a dialkyl carbonate represented by the following formula (C):

(C)

wherein $R^2$ is as defined for formula (B) above, and a diol represented by the following formula (D):

(D)

wherein $R^1$ is as defined for formula (A) above, while continuously withdrawing a low boiling point mixture in a gaseous form containing the produced dialkyl carbonate (C) and the unreacted aliphatic monohydric alcohol (B) from an upper portion of said multi-stage distillation column and continuously withdrawing a high boiling point mixture in a liquid form containing the produced diol (D) and the unreacted cyclic carbonate (A) from a lower portion of said multi-stage distillation column, and (2) continuously feeding said high boiling point mixture withdrawn from the lower portion of said multi-stage distillation column in step (1) to a continuous etherification reactor, to thereby effect a continuous etherification reaction between said unreacted cyclic carbonate (A) and a part of said produced diol (D) and produce a chain ether represented by the following formula (E):

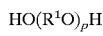
(E)

wherein $R^1$ is as defined for formula (A) above and p is an integer of from 2 to 4, and carbon dioxide, while continuously withdrawing the resultant etherification reaction mixture containing the remainder of the diol (D) produced in step (1) and the produced chain ether (E) from said continuous etherification reactor, said etherification reaction mixture having a cyclic carbonate content of from 0 to $10^{-2}$ in terms of the weight ratio of the cyclic carbonate (A) to the diol (D).

2. The method according to claim 1, wherein the conversion of said cyclic carbonate in the transesterification in step (1) is 50% or more.

3. The method according to claim 2, wherein the conversion of said cyclic carbonate in the transesterification in step (1) is from 95 to 99.999%.

4. The method according to any one of claims 1 to 3, wherein, in step (2), said continuous etherification reaction is conducted in the presence of an etherification catalyst.

5. The method according to any one of claims 1 to 3, wherein the conversion of said cyclic carbonate in the continuous etherification reaction in step (2) is from 90 to 100%.

6. The method according to any one of claims 1 to 3, wherein said etherification reaction mixture withdrawn from said continuous etherification reactor in step (2) contains said carbon dioxide, and wherein said carbon dioxide is removed from said etherification reaction mixture.

7. The method according to any one of claims 1 to 3, wherein said aliphatic monohydric alcohol used in step (1) contains a concomitant dialkyl carbonate in an amount of from 0 to 40% by weight, based on the total weight of said aliphatic monohydric alcohol and said concomitant dialkyl carbonate.

8. The method according to any one of claims 1 to 3, wherein said high boiling point mixture withdrawn from the lower portion of said continuous multi-stage distillation column in step (1) contains a part of the unreacted aliphatic monohydric alcohol, and wherein said high boiling point mixture is continuously introduced, prior to the feeding thereof to said continuous etherification reactor in step (2), to a low boiling point mixture separation column which is comprised of a continuous multi-stage distillation column, and wherein a low boiling point mixture containing said part of the unreacted aliphatic monohydric alcohol which is contained in said high boiling point mixture is continuously withdrawn from an upper portion of said low boiling point mixture separation column, while continuously withdrawing a high boiling point mixture containing said diol (D) and said unreacted cyclic carbonate (A) from said low boiling point mixture separation column through one or more side-cut withdrawal ports provided in a side wall of said column at one or more positions thereof corresponding to one or more stages selected from the group consisting of intermediate stages and a lowermost stage of said low boiling point mixture separation column, wherein said low boiling point mixture withdrawn from the upper portion of said low boiling point mixture separation column is continuously recycled to said multi-stage distillation column used in step (1), while continuously feeding said high boiling point mixture withdrawn through said side-cut withdrawal port of said low boiling point mixture separation column to said continuous etherification reactor used in step (2).

9. The method according to any one of claims 1 to 3, wherein said high boiling point mixture withdrawn from the lower portion of said continuous multi-stage distillation column in step (1) contains a part of the unreacted aliphatic monohydric alcohol, and wherein said high boiling point mixture is continuously introduced, prior to the feeding thereof to said continuous etherification reactor in step (2), to a low boiling point mixture separation column which is comprised of a continuous multi-stage distillation column, and wherein a low boiling point mixture containing said part of the unreacted aliphatic monohydric alcohol which is contained in said high boiling point mixture is continuously withdrawn from an upper portion of said low boiling point mixture separation column, while continuously withdrawing a high boiling point mixture containing said diol (D) and said unreacted cyclic carbonate (A) from a lower portion of said low boiling point mixture separation column, wherein said low boiling point mixture withdrawn from the upper portion of said low boiling point mixture separation column is continuously recycled to said multi-stage distillation column used in step (1), while continuously feeding said high boiling point mixture withdrawn from the lower portion of said low boiling point mixture separation column to said continuous etherification reactor used in step (2).

10. The method according to any one of claims 1 to 3, wherein said high boiling point mixture withdrawn from the lower portion of said continuous multi-stage distillation column in step (1) contains a part of the unreacted aliphatic monohydric alcohol, and wherein said high boiling point mixture is continuously introduced to a low boiling point mixture separation/etherification column which is comprised of a continuous multistage distillation column having a lower portion thereof adapted for serving as said continuous etherification reactor used in step (2), and wherein said continuous etherification reaction between said unreacted cyclic carbonate (A) and said diol (D) is effected in said lower portion of said low boiling point mixture separation/etherification column to produce said chain ether (E) and said carbon dioxide, while continuously withdrawing a low boiling point mixture containing said carbon dioxide and containing said part of the unreacted aliphatic monohydric alcohol which is contained in said high boiling point mixture from an upper portion of said low boiling point mixture separation/etherification column and continuously withdrawing a high boiling point mixture comprising the etherification reaction mixture containing the remainder of the diol (D) produced in step (1) and the produced chain ether (E) from said lower portion of said low boiling point mixture separation/etherification column, wherein said low boiling point mixture withdrawn from the upper portion of said low boiling point mixture separation/etherification column is continuously recycled to said multi-stage distillation column used in step (1).

11. The method according to any one of claims 1 to 3, wherein said cyclic carbonate is ethylene carbonate and said aliphatic monohydric alcohol is selected from the group consisting of methanol, ethanol, n-propanol, iso-propanol, n-butanol, iso-butanol, sec-butanol and tertbutanol.

12. The method according to any one of claims 1 to 3, wherein said cyclic carbonate is ethylene carbonate, said aliphatic monohydric alcohol is methanol and said chain ether is diethylene glycol.

* * * * *